United States Patent
Vercellotti et al.

(10) Patent No.: US 12,114,870 B1
(45) Date of Patent: Oct. 15, 2024

(54) OSTEOTOMY METHOD AND INSTRUMENTS

(71) Applicants: Tomaso Vercellotti, Genoa (IT); Alberto Rebaudi, Genoa (IT)

(72) Inventors: Tomaso Vercellotti, Genoa (IT); Alberto Rebaudi, Genoa (IT)

(73) Assignee: Rex Implants, LLC, Columbus, OH (US)

( * ) Notice: Subject to any disclaimer, the term of this patent is extended or adjusted under 35 U.S.C. 154(b) by 213 days.

(21) Appl. No.: 15/940,275

(22) Filed: Mar. 29, 2018

(51) Int. Cl.
| | |
|---|---|
| *A61C 1/12* | (2006.01) |
| *A61B 17/16* | (2006.01) |
| *A61C 1/07* | (2006.01) |
| *A61C 8/00* | (2006.01) |

(52) U.S. Cl.
CPC ........... *A61B 17/1673* (2013.01); *A61C 1/07* (2013.01); *A61C 1/12* (2013.01); *A61C 8/0089* (2013.01)

(58) Field of Classification Search
CPC ......... A61B 17/1673; A61C 1/12; A61C 1/07; A61C 8/0089
See application file for complete search history.

(56) References Cited

U.S. PATENT DOCUMENTS

| | | | | |
|---|---|---|---|---|
| 2,990,616 A | * | 7/1961 | Kuris | .................... B29C 66/861 |
| | | | | 433/119 |
| 3,636,943 A | * | 1/1972 | Balamuth | ............... A61B 17/11 |
| | | | | 601/2 |
| 3,729,825 A | | 5/1973 | Linkow et al. | |
| 3,905,109 A | | 9/1975 | Cohen et al. | |
| 3,950,850 A | | 4/1976 | Driskell et al. | |
| 4,177,562 A | | 12/1979 | Miller et al. | |
| 4,571,184 A | * | 2/1986 | Edwardson | ............... A61C 3/06 |
| | | | | 433/166 |
| 4,573,922 A | | 3/1986 | Bello | |
| 4,713,003 A | | 12/1987 | Symington | |

(Continued)

FOREIGN PATENT DOCUMENTS

| | | |
|---|---|---|
| DE | 24 54414 A1 | 5/1975 |
| EP | 0 361 526 A3 | 4/1990 |

(Continued)

OTHER PUBLICATIONS

International Search Report for PCT/EP2010/069003 dated Mar. 25, 2011.

(Continued)

*Primary Examiner* — Ralph A Lewis

(74) *Attorney, Agent, or Firm* — Jason H. Foster; Kremblas & Foster

(57) ABSTRACT

A method of forming a cavity in bone, the cavity formed and instruments used to form the cavity with an ultrasonic, piezoelectric surgical device for subsequent insertion of a blade implant. The method includes inserting instruments into a cavity to abrade the bone and shape the thickness of the cavity to be equal to or smaller than the implant. The cavity is formed with a generally tapered shape with at least one necked-down portion that may be in a trabecular bone. The instruments include a tip having a working portion with faces angled relative to one another and surface formations that abrade a cavity sidewall surface when moved rapidly and held against the surface.

5 Claims, 19 Drawing Sheets

(56) References Cited

U.S. PATENT DOCUMENTS

| | | | |
|---|---|---|---|
| 4,731,019 A * | 3/1988 | Martin | A61C 1/07 |
| | | | 433/119 |
| 4,762,492 A | 8/1988 | Nagai | |
| 4,799,886 A | 1/1989 | Wimmer | |
| 4,997,383 A | 3/1991 | Weiss et al. | |
| 5,102,336 A | 4/1992 | Linkow | |
| 5,116,226 A | 5/1992 | Linkow | |
| 5,971,758 A * | 10/1999 | Hugo | A61B 17/1615 |
| | | | 433/118 |
| 6,910,889 B1 * | 6/2005 | Hickok | A61C 3/03 |
| | | | 433/119 |
| 6,921,264 B2 | 7/2005 | Mayer et al. | |
| 7,303,396 B2 | 12/2007 | Abarno | |
| D576,729 S * | 9/2008 | Tanaka | D24/144 |
| 8,353,912 B2 * | 1/2013 | Darian | A61B 17/320068 |
| | | | 606/279 |
| D750,781 S * | 3/2016 | Tanaka | D24/152 |
| 9,566,136 B2 * | 2/2017 | Vercellotti | A61C 8/0019 |
| 2002/0072034 A1 * | 6/2002 | Hickok | A61C 3/03 |
| | | | 433/119 |
| 2003/0087217 A1 | 5/2003 | Coatoam | |
| 2004/0023187 A1 * | 2/2004 | Hickok | A61C 3/03 |
| | | | 433/119 |
| 2004/0038180 A1 | 2/2004 | Mayer et al. | |
| 2004/0053196 A1 | 3/2004 | Mayer et al. | |
| 2006/0216673 A1 | 9/2006 | Park | |
| 2006/0292526 A1 | 12/2006 | Simmons, Jr. | |
| 2009/0061389 A1 | 3/2009 | Lomicka et al. | |
| 2013/0171582 A1 * | 7/2013 | Nishikibe | A61C 17/0202 |
| | | | 433/86 |
| 2013/0204285 A1 * | 8/2013 | Gouery | A61B 17/320068 |
| | | | 606/169 |
| 2016/0089217 A1 * | 3/2016 | Gyurko | A61C 8/0019 |
| | | | 433/118 |
| 2019/0183521 A1 * | 6/2019 | Li | A61B 17/16 |

FOREIGN PATENT DOCUMENTS

| | | |
|---|---|---|
| JP | 61 176339 | 8/1986 |
| WO | 2004 017857 A1 | 3/2004 |
| WO | 2011 069978 A1 | 6/2011 |
| WO | 2018040917 A1 | 8/2018 |

OTHER PUBLICATIONS

Written Opinion of the International Searching Authority for PCT/EP2010/069003 dated Mar. 25, 2011.

* cited by examiner

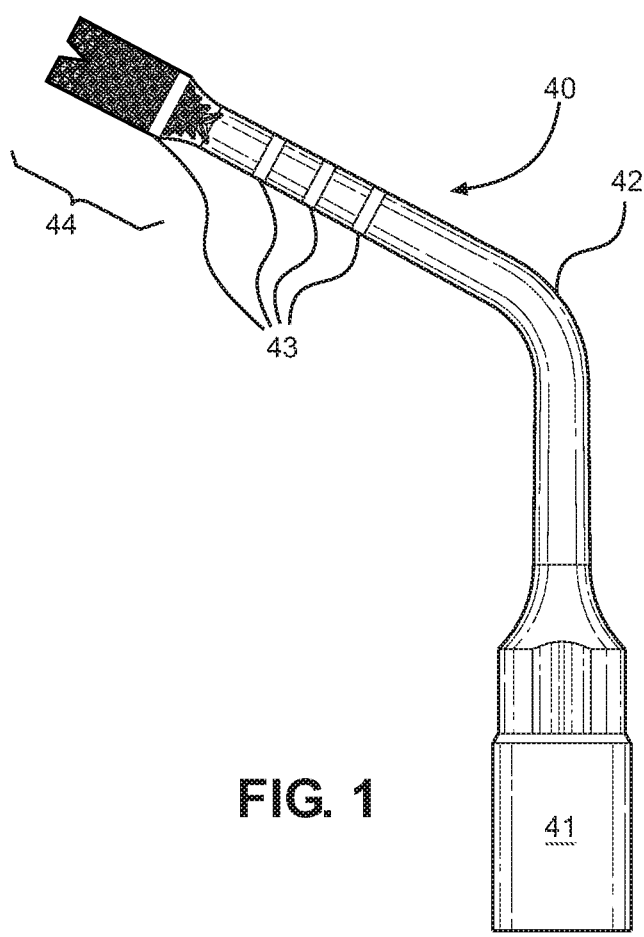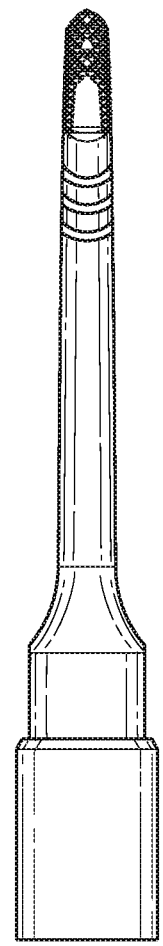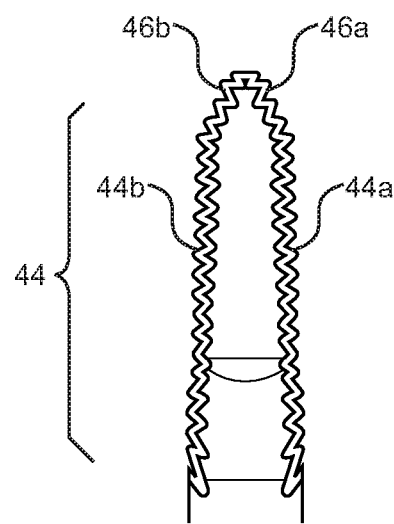
FIG. 1
FIG. 2
FIG. 3

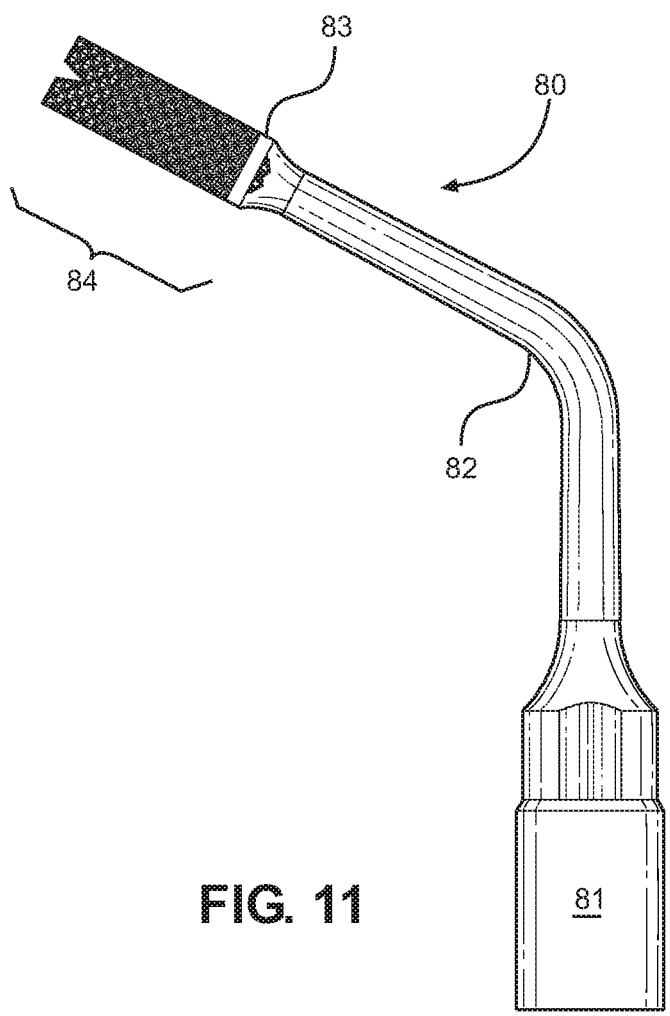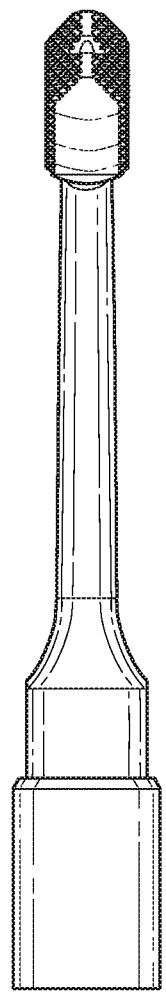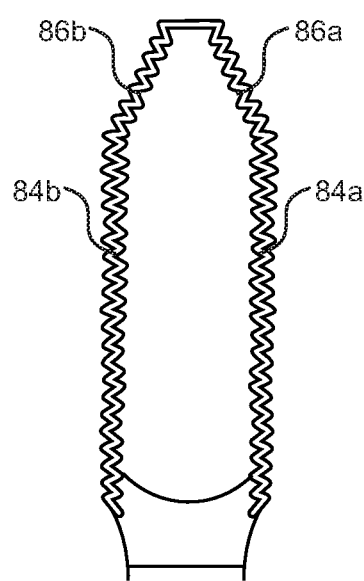
FIG. 11
FIG. 12
FIG. 13

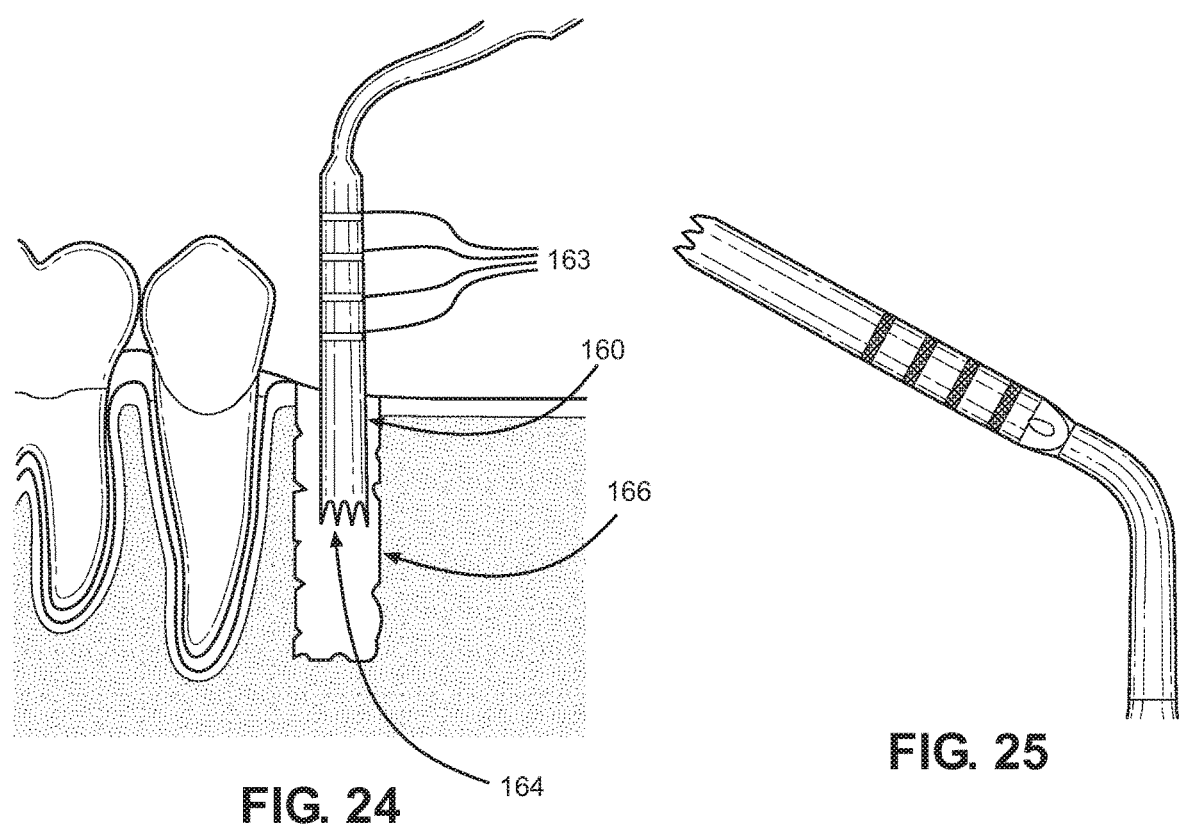
FIG. 24
FIG. 25
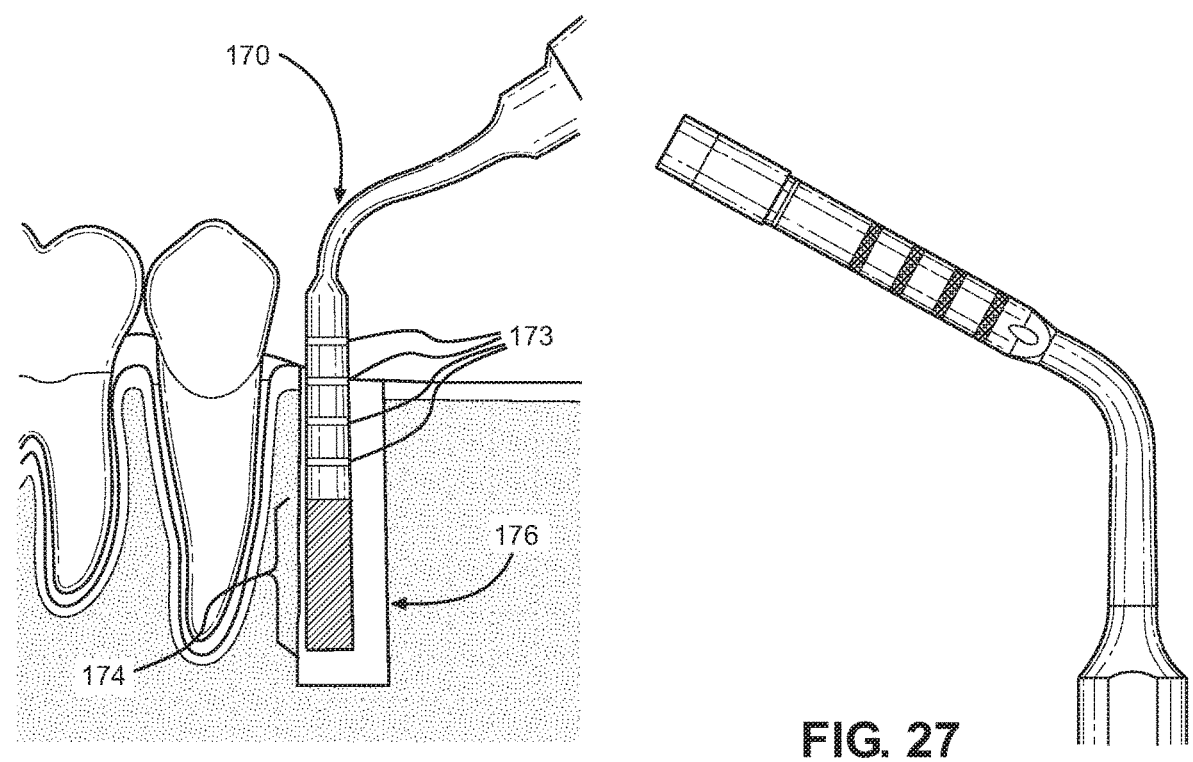
FIG. 26
FIG. 27

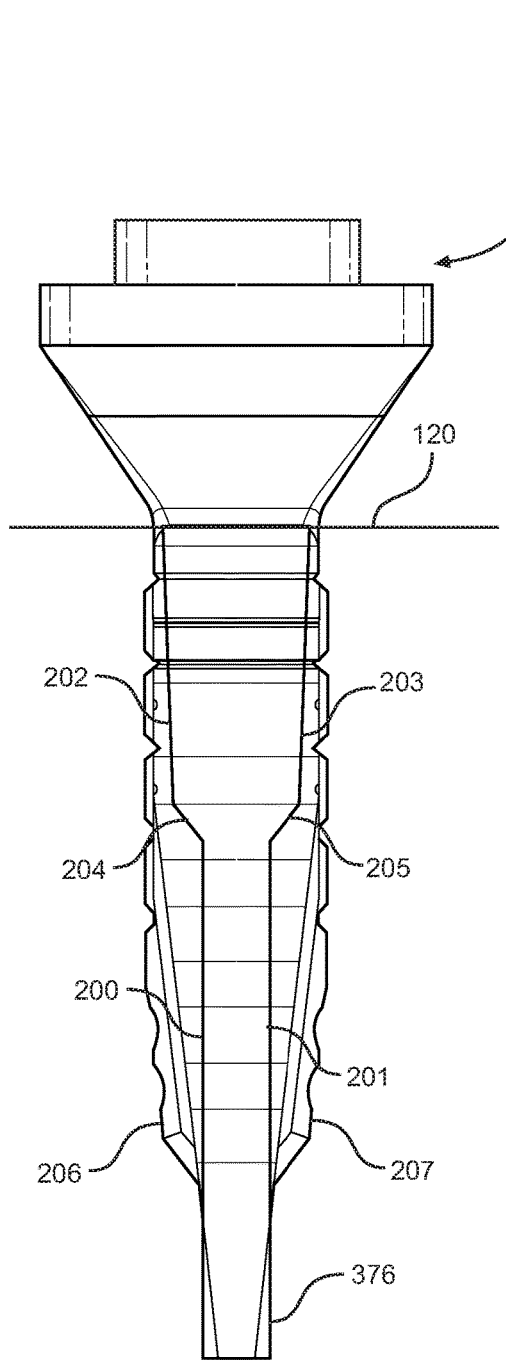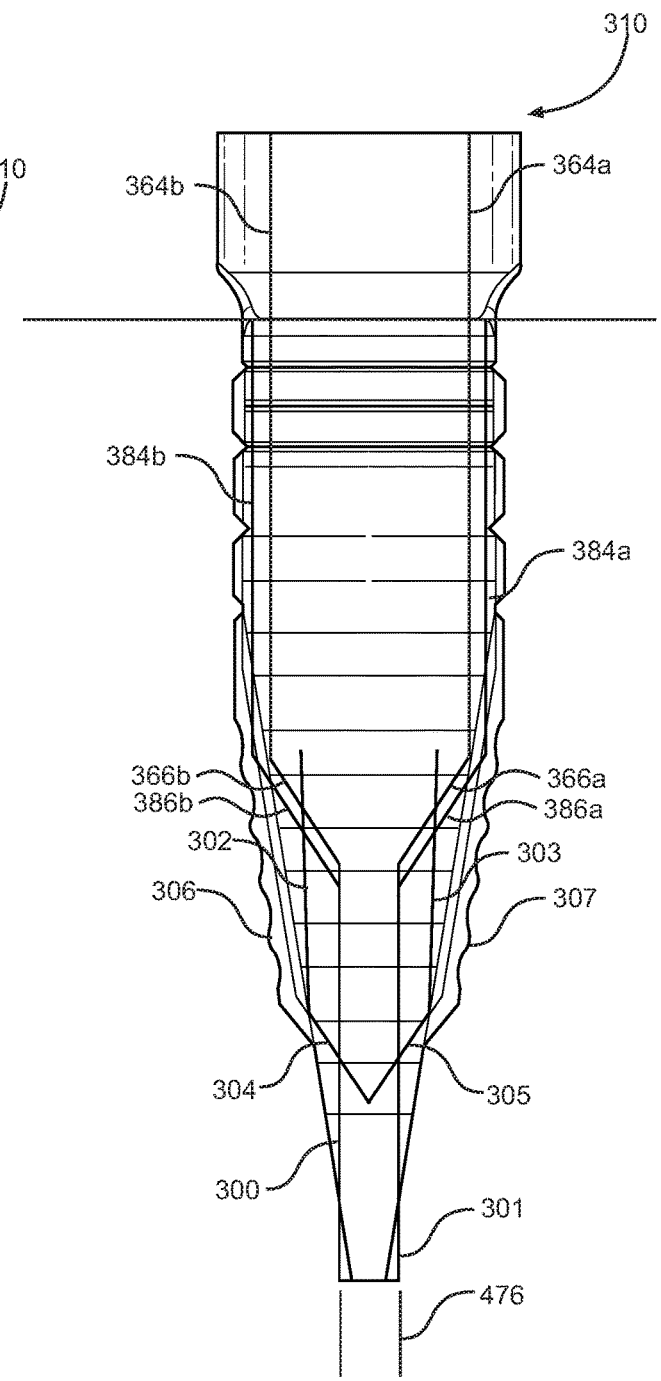
FIG. 34
FIG. 35

OSTEOTOMY METHOD AND INSTRUMENTS

BACKGROUND OF THE INVENTION

This invention relates generally to methods and instruments for installing implants in bone, and more particularly to methods and instruments for forming cavities in the bones of the mouth into which dental implants may be inserted.

It is well known that humans and animals lose teeth and have teeth that are damaged by disease, neglect, and injury. At times, damaged and lost teeth must be replaced to avoid further degeneration or movement of adjoining teeth, in addition to discomfort and emotional difficulties that may result from a loss of one or more teeth. A traditional manner of replacing one or more teeth is to mount one or more replacement teeth to adjoining teeth or their roots via a bridge. However, bridges and their attached dentures have disadvantages, and sometimes there is no adjacent tooth to function as a mount.

A dental implant with an attached prosthesis may replace an individual tooth by inserting an implant fixture into the bone of the mouth and then attaching a prosthesis onto the implant fixture. As an optional step an abutment may be attached to the implant fixture prior to attaching the prosthesis. The finished product looks and serves much like a tooth because it has a root-like, elongated portion that extends deep into the bone. Dental implants are traditionally installed by forming a cylindrical void in the bone and then installing a cylindrically-shaped implant in the void. Such implants have sharp, helical threads that extend around the exterior of the implant in the manner of a screw. The implants are thus "screwed" into the voids so that the threads cut slightly into the bone. These threads in the bone maintain the implant in position until substantial bone growth can take place around the rest of the implant. Some cylindrical implants have no threads, but instead are press-fit into cylindrical holes that are slightly smaller than the implants.

Cylindrical voids or cavities are typically formed in bone by using a drill in a conventional manner to cut and remove bone particles from the bone. Some bones are too narrow to form a cylindrical void while leaving sufficient bone to support an insert. Blade implants, which are non-circular, and commonly rectangular, in cross-section and have a generally wedge shape, may be used. Because blade implants have a much greater width than thickness, they provide sufficient surface area to resist movement against typical chewing forces. Thus, such blade implants are often used when a narrow bone must receive an implant.

One disadvantage of blade implants is that a drill cannot form a void with an elongated cross-sectional shape needed to insert a blade implant. Therefore, drills are not used to form a void for a blade implant in a narrow bone. Instead, surgeons typically must form a void using scalpels or a combination of scalpels and drills. Once the void is formed, the blade implant is forced into the void.

There are many difficulties with scalpel-cut voids, but these include forming a void that is the incorrect size and shape for the blade implant. If the void is too large, the implant may not be held in place while the bone grows around the implant. If the void is too small, the bone may break if the implant is inserted with too much force. Only if the void has an adequate degree of underpreparation in relation to the relative degree of bone mineralization at the implant site will the implant be prevented from moving before bone growth occurs and will the implant avoid breaking the bone during insertion.

There is some teaching in the prior art to use a piezoelectric device to vibrate cutting tools at high frequency and low amplitude to cut bone to form a void. There is also some teaching to use such piezoelectric devices to cut elongated voids using tips of strategic sizes and shapes. However, conventional cutting tools used with piezoelectric devices do not give the kind of precision that is desired to form a void of a shape and size that is desirably related to the blade implant, where the void is the correct sizes in the correct places. Thus, the need exists for a method and instruments used to form an exact-size and shape osteotomy void for a blade implant.

BRIEF SUMMARY OF THE INVENTION

Described herein are endosseous dental implants, surgical instruments, restorative components, methods of forming cavities or voids, voids formed using the instruments and using the methods, and methods of inserting implants. All implants, instruments and components are made in a variety of dimensions to accommodate differing patient anatomy, and it will be apparent to a person of ordinary skill from this description that not all possible variations are described herein. All methods are carried out taking differing patient anatomy into consideration, and the practitioner, who may be a surgeon, will understand from the description herein how to make modifications to accommodate different patient anatomy and tissue conditions.

The instruments are used to create a cavity into which an implant is inserted, and the cavity may be formed in the maxillary or mandibular bone. Once sufficient healing has occurred, or immediately after insertion of the implant, a prosthesis may be mounted, directly to the implant or via an abutment, near the surface of the bone/soft tissue juncture. This prosthesis functions substantially similarly to a tooth, but it is contemplated that a prosthesis may be used that serves as multiple teeth or other functions that will be apparent to the person of ordinary skill.

The endosseous implants are preferably non-circularly-shaped in cross-section, and may have an overall wedge form with a taper from one end to the opposite end, possibly with interruptions in the tapered shape. An apical surface may be treated with resorbable blast media, which may be grit-blasted and/or acid passivated. Additional surface treatments are also contemplated including titanium plasma spray, acid etching, titanium oxide, sandblasting, or any combination. The implants may be in a variety of buccolingual thicknesses and lengths, and examples are thicknesses of 1.8 mm and 2.9 mm and lengths which range from about 4 mm to about 15 mm. The implants may have widths from about 4 mm to about 20 mm. Of course, these are not the only lengths, thicknesses, widths and shapes, but these examples represent common sizes and shapes. Examples of the implant used herein are described in U.S. Pat. No. 9,566,136 to Vercellotti et al., which is incorporated herein by reference. A person of ordinary skill will understand from the disclosure herein how to modify the procedures and structures to accommodate different size and shape implants.

One instrument used with the methods described herein is a dental piezoelectric ultrasonic surgical device that uses ultrasonic energy to generate mechanical microvibration of insert tips intended for bone cutting and for general scaling treatments. Piezoelectric devices of this type are described in U.S. Pat. No. 8,002,783 to Vercellotti et al., which is incorporated herein by reference. U.S. Pat. No. 8,109,931 to Vercellotti et al., U.S. Pat. No. 8,808,295 to Vercellotti et al., and U.S. Pat. No. 6,695,847 to Bianchetti et al. show instruments and devices that may be used in the methods described herein, and are likewise incorporated herein by reference.

The piezoelectric ultrasonic surgical device may include a table-top console containing an irrigation delivery system, an internal electric power supply, a control keyboard, and an ultrasonic generator. The device also includes a foot-pedal and a piezoelectric ultrasonic hand-piece, which may be connected to the console by means of cords. Described herein are a variety of tip inserts designed with different morphology/shape to be used for different dental procedures, which may be mounted to the hand-piece in a conventional manner and used by a practitioner. The practitioner may use the tips described herein in a manner described below, and in any other manner that the person of ordinary skill will understand from using existing tips in the hand-piece.

The implants described herein interact differently with different parts of the bone, and the osteotomy's shape and size are formed to cooperate with each implant in such a way that the combination provides benefits over the prior art.

There may be three regions of the osteotomy void where there is an important relationship between the void and the implant. First, at the coronal end where the cortical bone is most dense, the thickness of the void is between about 0.0 and 0.4 mm thinner than the implant for a 1.8 to 2.9 mm thick implant. This difference extends down about 3.5 mm from the opening of the void, but can be more or less. The difference at the spongy, trabecular bone may be higher than at the cortical bone, and may be as high as about 0.9 to 1.3 mm.

Second, there is a difference in dimensions where the bone transitions from cortical to trabecular. At this transition point, which may occur between 0.1 and 5.5 mm from the opening of the osteotomy, the void is about 0.9 to 1.0 mm narrower than the implant in thickness, and it is preferred to form a necked-down region at this point.

Third, at the apical end, which is the deepest region of the osteotomy cavity, the implant may be thicker or thinner than the void and deeper than, or not as deep as, the cavity's deepest extent. Of course, the bone quality density and the embodiment (e.g., implant shape morphology) can affect these variations. For example, the bone may be more dense and may transition to a cortical structure toward the apical end of the cavity. Thus a more "gentle" press-fit may be desired with variations at the apical end. The relationship between the implant, the cavity and the bone characteristics should be considered by the clinician to permit easy insertion of the implant to the osteotomy.

Disclosed herein is an elongated cavity in a bone defined by sidewalls formed within the bone. The cavity comprises an opening end in a cortical region of the bone and an apical end in a trabecular or cortical region of the bone. The cavity has a cavity length extending between the opening end and the apical end along which a longitudinal axis extends. The cavity length and a cavity width are greater than a cavity thickness that varies along the cavity length. The cavity thickness is greater at the opening end than at the apical end. The cavity includes at least a first necked-down portion over a first segment of the cavity length in which a first per unit length change in cavity thickness in the first segment's length exceeds a per unit length change in cavity thickness along the cavity length. The cavity has a non-circular cross section through the plane perpendicular to the longitudinal axis. The cavity may have a second necked-down portion in which a second per unit length change in cavity thickness exceeds the per unit length change in cavity thickness along the cavity length. The first and second necked-down regions may be formed in the trabecular region of the bone.

In one embodiment, an implant may be inserted in the cavity. The implant may have an implant length and an implant width that are greater than an implant thickness. The implant thickness may exceed the cavity thickness at least at some locations along the implant length, whereby the implant displaces the sidewalls of the cavity during insertion so that the implant thickness equals a post-insertion cavity thickness at least at some points along the cavity length. A cavity may have the same length and width as the implant that will be inserted therein in order for insertion to proceed well. Furthermore, the thickness of a cavity may be slightly less than the thickness of the implant that will be inserted therein to provide stability at the time of insertion due to frictional engagement between the implant and the sidewalls that define the cavity.

Disclosed herein is a tip for attaching to an instrument that vibrates at ultrasonic frequency. The tip may have a base for attaching to the instrument and a shaft extending from the base to a tip end. The tip includes a working portion disposed on the shaft opposite the base. The working portion includes at least first and second opposing faces defining the terminal end of the working portion and forming an angle relative to one another between about 60 degrees and 90 degrees. The working portion also includes at least third and fourth opposing faces disposed between the first and second faces and the base, the third and fourth faces angled relative to one another between about 0.0 to degrees and 2.0 degrees. At least the first and second, and possibly also the third and fourth, faces have surface formations configured to abrade bone when one of said faces contacts bone during vibration.

Disclosed herein is an osteotomy method that includes a step of forming an elongated cavity in a bone, wherein the cavity is defined by spaced sidewalls. The cavity has a cavity length and a cavity width that are greater than a cavity thickness. An opening end is formed in a cortical region of the bone and an apical end is formed in a trabecular region of the bone or, alternatively, in a cortical region of the bone. A longitudinal axis extends between the opening end and the apical end. The cavity has a non-circular cross section through a plane perpendicular to the longitudinal axis. Another step includes attaching a removable tip to an instrument that is configured to vibrate the tip at ultrasonic frequency. The tip has a base that attaches to the instrument and a tip shaft extending from the base to a working portion. The working portion includes first and second opposing faces defining the terminal end of the tip and forming an angle relative to one another between about 60 degrees and 90 degrees. The working portion also includes third and fourth opposing faces disposed between the first and second faces and the base, the third and fourth faces angled relative to one another between about 0.0 degrees and 2.0 degrees. At least the first and second, and possibly also the third and fourth, faces have surface formations that result in the abrasion of bone when one of said faces contacts bone during vibration. Yet another step includes inserting the working portion of the tip into the cavity and seating the first, second, third and fourth faces against the cavity sidewalls while the instrument vibrates the tip. This thereby abrades the sidewalls to make the cavity thickness greater at the opening end than at the apical end and forms at least a first necked-down portion over a first segment of the cavity length. In the necked-down portion a first per unit length change in cavity thickness in the first segment's length exceeds a per unit length change in cavity thickness along the cavity length.

In one embodiment, a second tip, having angled or parallel sidewalls, is inserted into the cavity to enlarge the necked-down portion. In another embodiment, a second tip may be inserted into the cavity to form a second necked-down portion. In another embodiment, an implant may be inserted into the cavity, thereby compressing the bone. The bone is preferably compressed along the entire length of the implant, and the trabecular bone may be compressed the most at the necked-down portion.

BRIEF DESCRIPTION OF THE SEVERAL VIEWS OF THE DRAWINGS

FIG. 1 is a side view illustrating a tip made in accordance with the present invention that is for use with a piezoelectric ultrasonic surgical device.

FIG. 2 is a front view illustrating the tip of FIG. 1.

FIG. 3 is a magnified edge view illustrating the extreme end of the tip of FIG. 1 showing the working portion thereof.

FIG. 11 is a side view illustrating an alternative tip embodiment made in accordance with the present invention that is for use with a piezoelectric ultrasonic surgical device.

FIG. 12 is a front view illustrating the tip of FIG. 11.

FIG. 13 is a magnified edge view illustrating the extreme end of the tip of FIG. 11 showing the working portion thereof.

FIG. 24 is a schematic side view in section through the line B-B of FIG. 17 illustrating a surgical step in which a micro-saw cuts through the bone to form an osteotomy cavity.

FIG. 25 is a side view illustrating the micro-saw of FIG. 24.

FIG. 26 is a schematic side view in section through the line B-B of FIG. 17 illustrating a surgical step in which a micro-file shapes the osteotomy cavity.

FIG. 27 is a side view illustrating the micro-file of FIG. 26.

FIG. 34 is a side view in section illustrating a first implant inserted into a cavity.

FIG. 35 is a side view in section illustrating a second implant inserted into a cavity.

Figure 4:
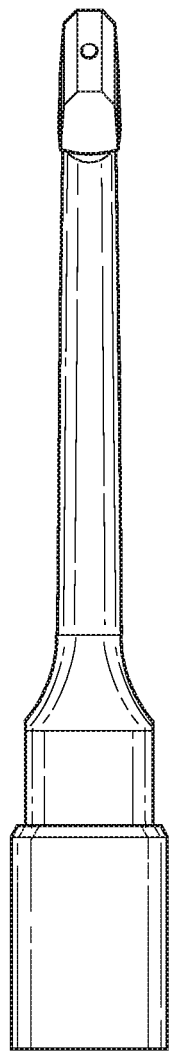
FIG. 4 is a front view illustrating the tip of FIG. 1 without the knurling on the working portion in order to more clearly illustrate the surface features of the working portion.
Figure 5:
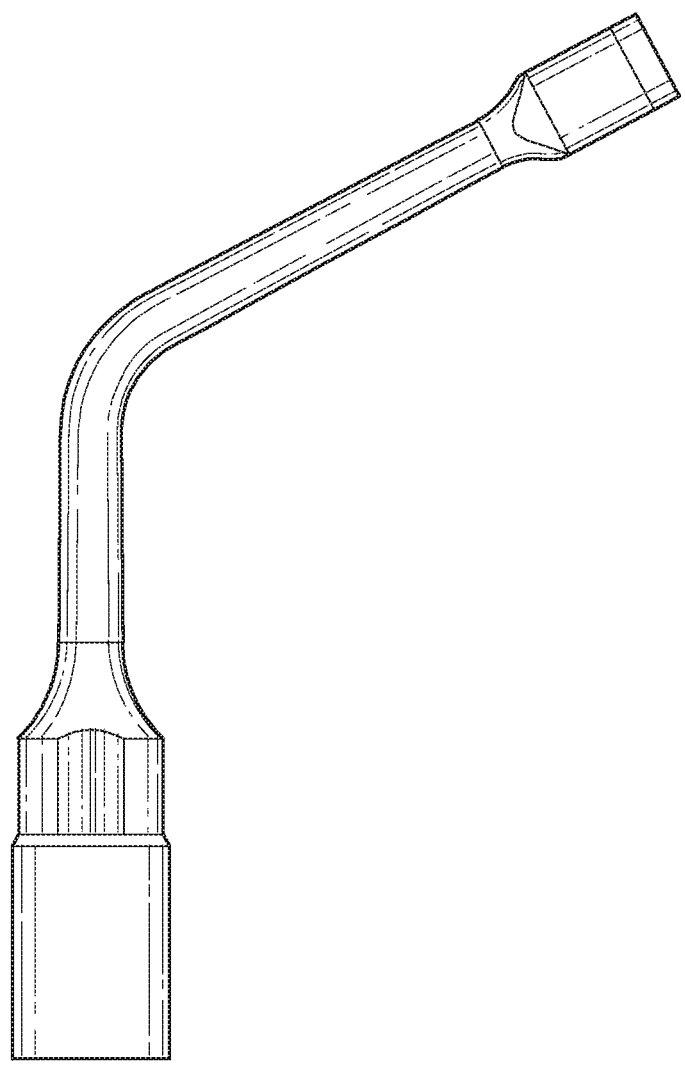
FIG. 5 is a side view illustrating the tip of FIG. 1 without the knurling on the working portion in order to more clearly illustrate the surface features of the working portion.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or terms similar thereto are often used. They are not limited to direct connection, but include connection through other elements where such connection is recognized as being equivalent by those skilled in the art.

DETAILED DESCRIPTION OF THE INVENTION

A variety of surgical instruments and other devices, such as implants, are described herein. Some of these instruments and devices are used in procedures that are described herein and in patents incorporated by reference. Furthermore, some of the instruments have uses that persons of ordinary skill will already be aware of and will understand from the description herein. Therefore, not all structures are described in the detail required by a person unfamiliar with the technology. Nevertheless, a person of ordinary skill will understand.

A file tip 40 is shown in FIGS. 1-5. The file tip 40 has a base 41 that mounts to a piezoelectric surgical device so that the piezoelectric device may vibrate the base 41, the integral shaft 42 and the working portion 44 of the shaft 42 that forms the terminal end thereof, distal from the base 41, in a manner that is known for various tips on piezoelectric instruments. Such vibration is known to cause the terminal end to act on living tissue, both soft and hard, for the purpose for which the terminal end was designed. As an example, a tip with a saw tooth terminal end will cut rapidly through bone when the vibrating terminal end is placed in contact with bone. In another example, a tip with diamond or other abrasive grit that is soldered or otherwise attached to the tip will abrade the bone when the vibrating terminal end is placed in contact with bone.

The terminal end of the file tip 40 preferably has a bi-bevel profile working portion 44 made up of at least two angled sections. A first angled section of the working portion 44 is preferably made up of opposing, non-parallel faces 44a and 44b, and a second angled section of the working portion is preferably made up of the opposing non-parallel faces 46a and 46b.

The face 44a preferably forms an angle relative to the face 44b of preferably less than 30 degrees, more preferably 1-25 degrees, and most preferably about 5-15 degrees. The faces 44a and 44b are close to, but not, parallel, thereby forming a tapered wedge.

The face 46a forms an angle relative to the face 46b of preferably less than 100 degrees, more preferably 45-90 degrees and most preferably 60 to 90 degrees. Thus, the faces 46a and 46b are at a substantial angle with one another to form a tapered wedge shape that is not substantially parallel, and form tapered regions in the cavities or voids as will be described below.

The file tip 40 is preferably made of metal, such as stainless steel, or any other medically-acceptable material, such as other metals, plastics, ceramics or composites, including an aggregate composite, such as metal with abrasive particles brazed, welded, sintered or otherwise mounted to the surface thereof. The implants, abutments, fit gauges, and other products described herein may be manufactured from a titanium alloy or any other medically-acceptable material, such as other metals, plastics, ceramics or composites. The file tip 40 may be used to enlarge a cavity during an osteotomy in a thickness direction as described in more detail below, particularly at or near the opening, but optionally in a deeper portion of the cavity.

The faces 44a, 44b, 46a and 46b have surface formations that form abrasive surfaces, as shown in FIGS. 1-3. The working portion 44 of the file tip 40 preferably has a diamond-pattern knurled surface with 0.6 mm wide ridges and similarly sized valleys between the ridges. Other types and sizes of knurling may be used, such as annular rings, linear, and straight, or combinations thereof. As is known, knurling involves deforming or removing portions of the surface of an article to provide abrasive characteristics to objects the article comes into contact with. Such surface formations are the same material throughout the article, and are to be distinguished from extremely hard particulate material that is brazed, adhered or otherwise bonded to an article. A common form of this is diamond particulate brazed or held by adhesive to an article. Such bonding of hard particulate to an article is not a surface formation, as defined herein, because it involves different material added to a surface rather than deforming or removing material from an article to leave a single material with surface structures that abrade when the surface structures are vibrated while held against a surface. Other surface treatments that increase abrasion by the file tip 40, but which may not be, strictly speaking, knurling, are contemplated. These include etching, among others. Diamond coating is considered a candidate for the invention technology, but this is not considered a surface formation.

Knurled surfaces are formed in a conventional manner, and the file tip 40 may be heat-treated after knurling to modify the hardness of the knurled surfaces. Knurling may be of various sizes, and the preferred size of the protruding ridges is about 0.6 mm wide. The grooves between the ridges are of a similar size. Knurling is one example of a surface formation that makes the surface of the working end of the tip able to better abrade bone, enlarge the initial osteotomy of the cavity and, thereby, prepare a precise implant site that may be undersized.

The thickness at the terminal end of the file tip 40 is about 0.6 mm and the faces 46a and 46b extend from this terminal end to a thickness (for the embodiment shown in FIG. 1) of about 1.4 mm. This is the maximum thickness of the first angled section made up of the faces 46a and 46b for a tip of this size, but of course other tip sizes are contemplated and will become apparent to the person of ordinary skill from this description. The faces 46a and 46b end and the faces 44a and 44b begin at the second angled section's farthest point from the base 41. The second angled section thus has a thickness that is about 1.4 mm at the end most distal from the base 41, and about 1.6 mm near the ends of the faces 44a and 44b that are closer to the base 41. The faces 46a and 46b may be about 1.0 mm long, and the faces 44a and 44b may be about 3.0 mm long. The working portion 44 may have a width of about 2.5 mm and a length of about 4.0 mm, but these dimensions are not critical. As an example, the tip 40 is suitable for the average human mouth. It will be understood that tips may have proportionally larger or smaller surfaces, and surface formations, when such tips are to be used in larger or smaller living organisms.

There are preferably indicia 43 formed on the file tip 40 indicating measured cutting depths of the file tip 40. These indicia may be about 0.5 mm wide (measured along the longitudinal axis of the file tip 40), and may be formed by any means, including ink or other coloring and/or surface structures, such as grooves extending into, or ridges extending out of, the file tip 40. Such surface structures may be formed by laser etching, machining, or any acceptable mechanism. The indicia 43 may be located on the file tip 40 at 4, 8, 10 and 12 mm from the terminal end of the file tip 40, and/or at any other location selected by the person of ordinary skill. Thus, the depth that the file tip 40 is extended into a void may be indicated by the indicia 43 so that the practitioner may determine how deep the file tip is by how many of the indicia 43, if any, are visible outside of the void, such as by being located at the opening of the void.

Figure 36A:
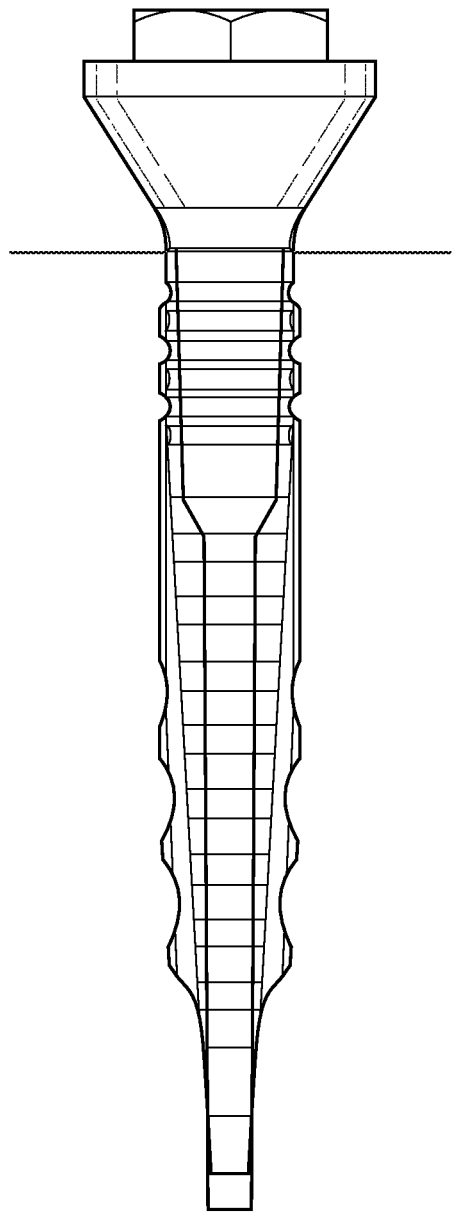
FIG. 36 is a side view in section illustrating a third implant inserted into a cavity.
Figure 36B:
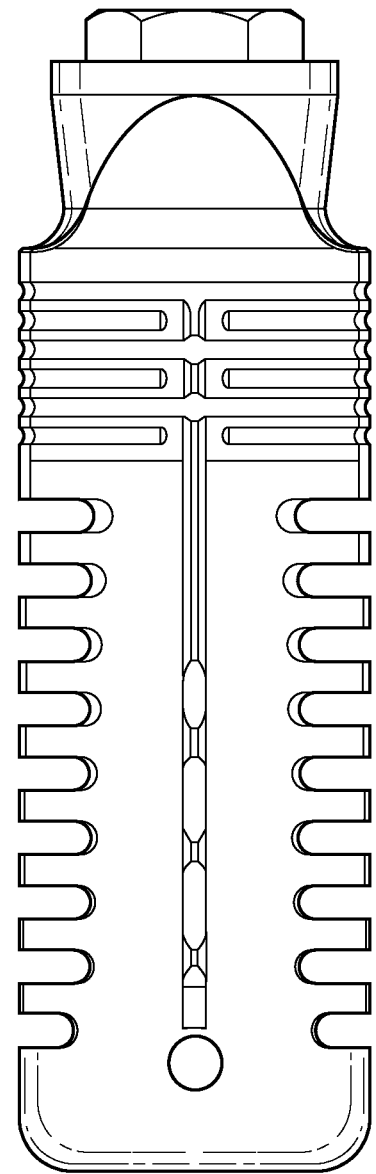

The file tip 40 may be used with the piezoelectric surgical hand-piece. When the working portion 44 contacts bone while being vibrated, such as at the opening and in deeper regions of the void formed as described below in more detail, the working portion 44 abrades the bone and thereby shapes and/or forms the sidewalls of the cavity formed during an osteotomy in a manner suitable for the cavity to receive an implant as described herein. The file tip 40 may have an irrigation canal that runs longitudinally therethrough, through which water or another fluid may be pumped to cool the bone during cutting. The irrigation canal may extend from the base 41 to an opening at the distal end of the working portion 44. Fluid may be pumped by the hand-piece through the irrigation canal along the length of the tip 40 and out of the distal end of the working portion 44. A cavitation effect may be caused by the fluid during cutting that may create an improved osteotomy. FIGS. 34-36 show implants in desired, corresponding osteotomy cavities. Below, Applicant describes the areas where the various file tips described herein may be used to shape the sidewalls in the bone that define the osteotomy cavity.

Another file tip 60 is shown in FIGS. 6-10. The file tip 60 has a base 61 that mounts to a piezoelectric surgical device so that the piezoelectric device may vibrate the base 61, the integral shaft 62 and the terminal end distal from the base 61 in a conventional manner. Such vibration is known to cause the terminal end to act on living tissue, both soft and hard, for the purpose for which the terminal end was designed in the same manner as with the tip 40, as described above.

The terminal end of the file tip 60 preferably has an abrasive working portion 64 with opposing, substantially-parallel faces 64a and 64b. The faces 64a and 64b are preferably substantially parallel, which is within about one degree of parallel. The working portion 64 also has opposing, non-parallel faces 66a and 66b that form a second, terminal end profile of a bi-bevel profiled work portion 64.

The face 66a forms an angle relative to the face 66b of preferably less than 100 degrees, more preferably 45-90 degrees and most preferably 60 to 90 degrees. Thus, the faces 66a and 66b form a tapered wedge shape at the terminal end of the working portion 84, which may be a first angled section of the working portion 64.

The file tip 60 is preferably made of metal, such as stainless steel, or any other medically-acceptable material, such as other metals, plastics, ceramics or composites, including an aggregate composite. The file tip 60 may be used to enlarge and shape an osteotomy cavity in a thickness direction as described in more detail below, particularly at or near the opening, but optionally in a deeper portion of the cavity.

Figure 6:
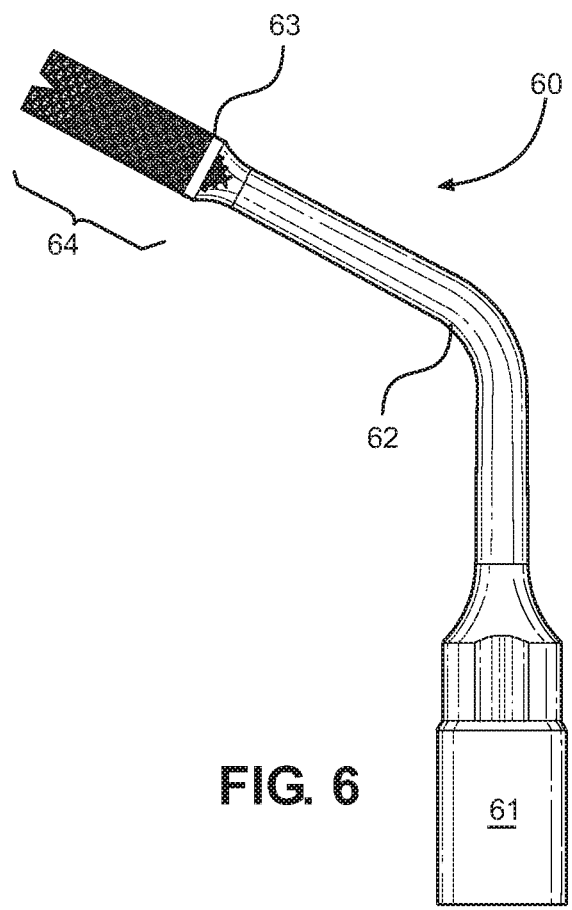
FIG. 6 is a side view illustrating an alternative tip embodiment made in accordance with the present invention that is for use with a piezoelectric ultrasonic surgical device.
Figure 7:
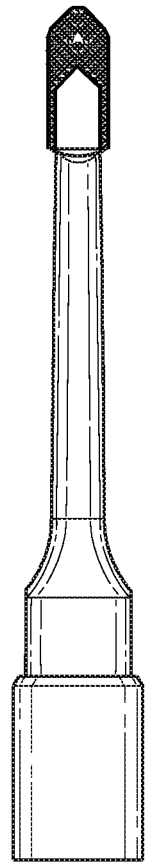
FIG. 7 is a front view illustrating the tip of FIG. 6.
Figure 8:
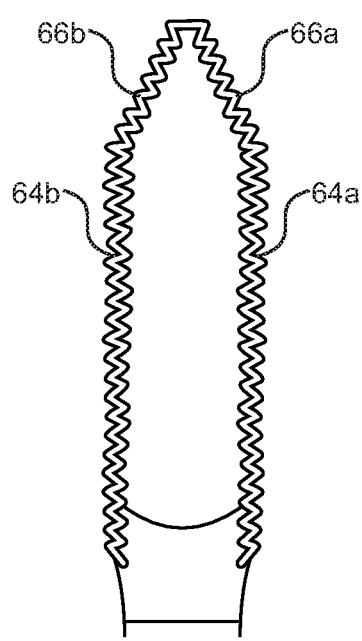
FIG. 8 is a magnified edge view illustrating the extreme end of the tip of FIG. 6 showing the working portion thereof.
Figure 9:
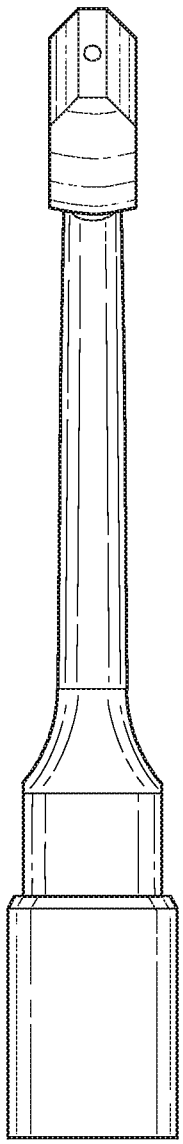
FIG. 9 is a front view illustrating the tip of FIG. 6 without the knurling on the working portion in order to more clearly illustrate the surface features of the working portion.
Figure 10:
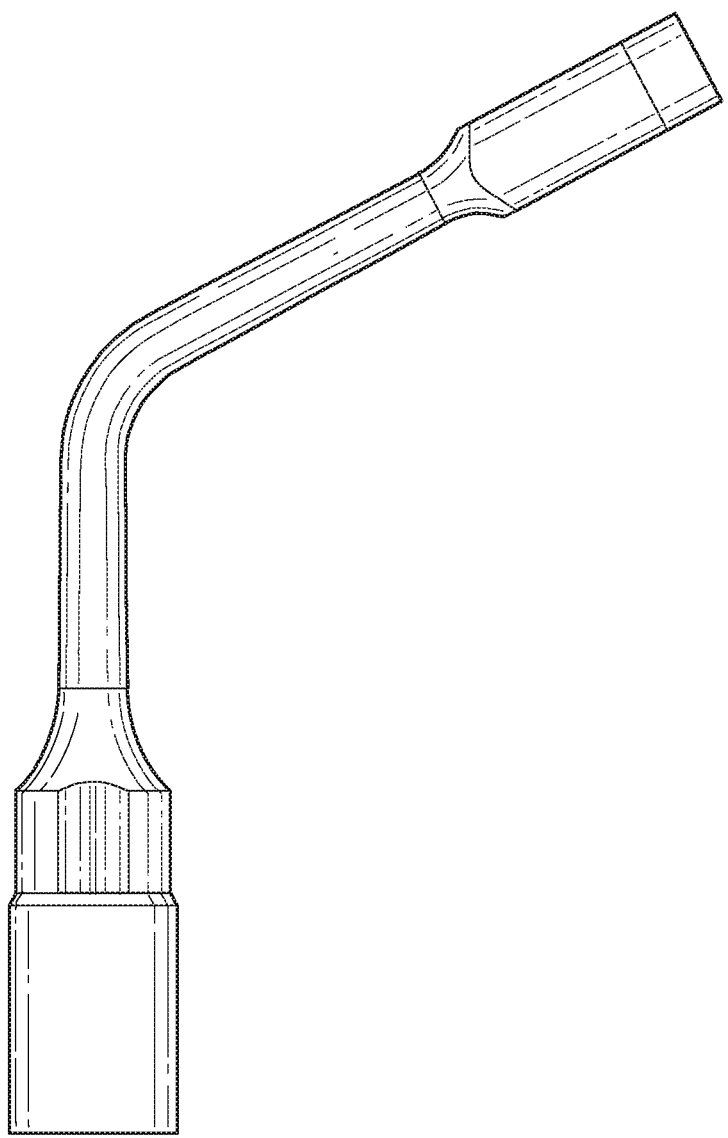
FIG. 10 is a side view illustrating the tip of FIG. 6 without the knurling on the working portion in order to more clearly illustrate the surface features of the working portion.
Figure 14:
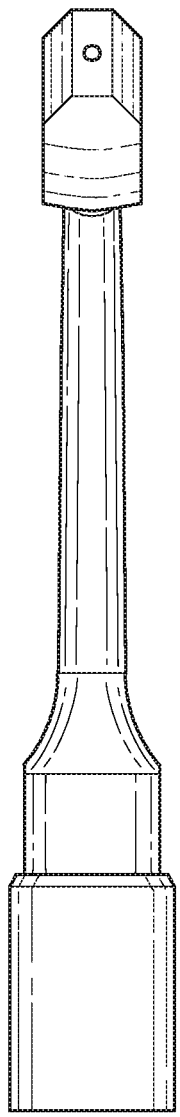
FIG. 14 is a front view illustrating the tip of FIG. 11 without the knurling on the working portion in order to more clearly illustrate the surface features of the working portion.
Figure 15:
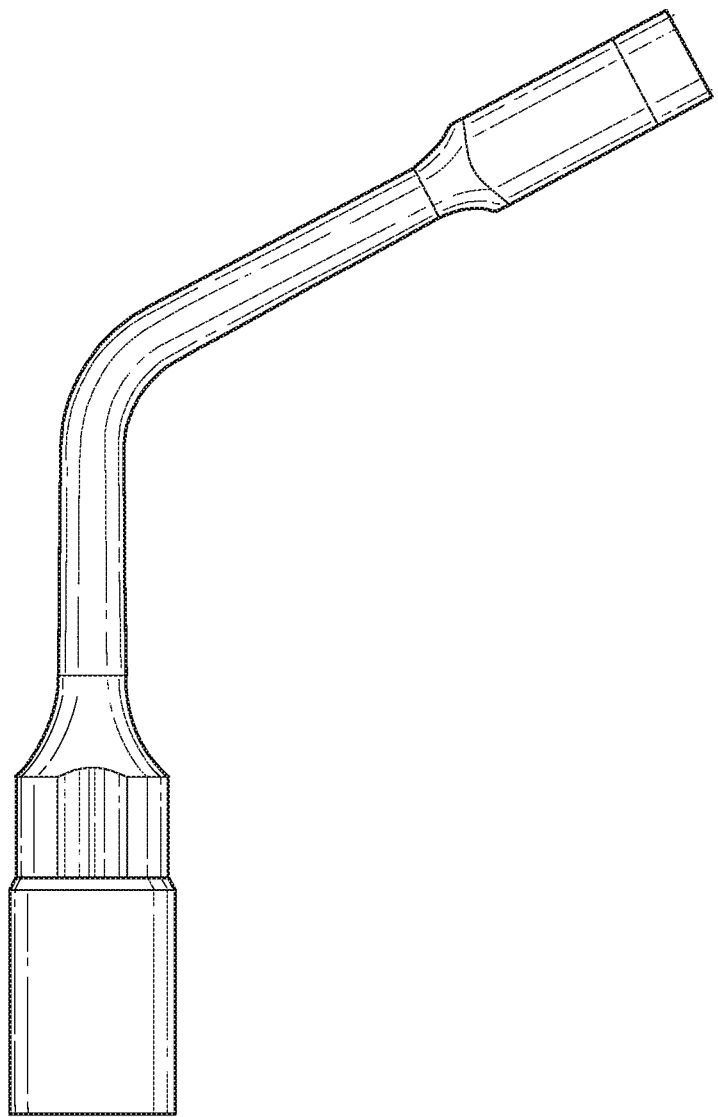
FIG. 15 is a side view illustrating the tip of FIG. 11 without the knurling on the working portion in order to more clearly illustrate the surface features of the working portion

The faces 64a, 64b, 66a and 66b have abrasive surface formations, as shown in FIGS. 6-8. The working portion 64 of the file tip 60 has a diamond-pattern knurled surface with 0.6 mm wide ridges, with similar characteristics to the knurling of the tip 40 described above, but this surface formation may be replaced by any other suitable surface formation.

The thickness of the working portion at the terminal end of the file tip 60 is about 0.7 mm and the faces 66a and 66b extend from this terminal end to a thickness (for the embodiment shown in FIG. 8) of about 2.3 mm. The faces 64a and 64b are spaced about 2.3 mm apart from the ends of the faces 64a and 64b that are closest to the faces 66a and 66b to the ends of the faces 64a and 64b that are closer to the shaft 62. In a preferred embodiment, the portion of the file tip 60 between the faces 64a and 64b is a consistent thickness, because the faces 64a and 64b are substantially parallel. However, alternatives are contemplated in which the faces 64a and 64b are non-parallel. The faces 66a and 66b may be about 1.9 mm long, and the faces 64a and 64b may be about 5.0 mm long. The working portion 64 may have a width of about 2.5 mm and a length of about 6.9 mm, but these dimensions are not critical. It will be understood that tips may have proportionally larger or smaller surfaces, and surface formations, when such tips are to be used with various living organisms of various sizes.

There is preferably at least one indicium 63 indicating the cutting depth of the file tip 60. This indicium may be about 0.5 mm wide (measured along the longitudinal axis of the tip 60), and may be formed by any means, including ink or other coloring on the file tip 60, or by grooves extending into, or bands extending out of, the file tip 60. The indicium 63 may be at about 7 mm from the terminal end of the file tip 60. Thus, the depth the file tip 60 extends into a void is indicated by the indicium 63, so the practitioner may determine how deep the file tip 60 extends by where the indicium 63 is relative to the opening to the void. Of course, more indicia may be placed on the file tip 60 to designate other tip cutting depths.

The file tip 60 is used to abrade bone at the opening and in deeper regions of the osteotomy void as described below, in order to shape the cavity that receives an implant. In general, the file tip 60 is used to abrade bone sidewalls in order to increase the thickness of the void, but this may be modified by the practitioner who is using the tip 60. The file tip 60 may have an irrigation canal that runs longitudinally therethrough, through which water or another fluid may be pumped to cool the bone during cutting. The irrigation canal may extend from the base 61 to an opening at the distal end of the working portion 64. Fluid may be pumped by the hand-piece through the irrigation canal along the length of the tip 60 and out of the distal end of the working portion 64. A cavitation effect may be caused by the fluid during cutting that may create an improved osteotomy. FIGS. 34-36 show implants with the desired, corresponding osteotomy voids. Below, Applicant describes the areas where the various file tips described herein may be used to shape the sidewalls that define the osteotomy void.

Another file tip 80 is shown in FIGS. 11-15. The file tip 80 has a base 81 that mounts to a piezoelectric surgical device so that the piezoelectric device may vibrate the base 81, the integral shaft 82 and the terminal end distal from the base 81 in a conventional manner. Such vibration is known to cause the terminal end to act on living tissue, both soft and hard, for the purpose for which the terminal end was designed. In the case of the tips 40, 60 and 80, the purpose of the design is to abrade bone to increase void thickness.

The terminal end of the file tip 80 preferably has an abrasive working portion 84 with opposing, substantially-parallel faces 84a and 84b, and opposing non-parallel faces 86a and 86b that form a bi-bevel profile. The faces 84a and 84b are substantially parallel, which is within about one degree of parallel.

The face 86a forms an angle relative to the face 86b of preferably less than 100 degrees, more preferably 45-90 degrees and most preferably 60 to 90 degrees. Thus, the faces 86a and 86b form a tapered wedge shape, which may be a first angled section of the working portion 84.

The file tip 80 is preferably made of metal, such as stainless steel, or any other medically-acceptable material, such as other metals, plastics, ceramics or composites, including an aggregate composite. The file tip 80 may be used to enlarge an osteotomy void in a thickness direction as described in more detail below, particularly at or near the opening, but optionally in a deeper portion of the void.

The faces 84*a*, 84*b*, 86*a* and 86*b* have abrasive surface formations, as shown in FIGS. 11-13. The working portion 84 of the file tip 80 has a diamond-pattern knurled surface with 0.6 mm wide ridges, but this surface formation may be replaced by any other suitable surface formation.

The thickness of the working portion at the terminal end of the file tip 80 is about 0.8 mm and the faces 86*a* and 86*b* extend from this terminal end to a thickness (for the embodiment shown in FIG. 13) of about 2.7 mm. The faces 84*a* and 84*b* are spaced about 2.7 mm apart from the ends of the faces 84*a* and 84*b* that are closest to the faces 86*a* and 86*b* to the ends of the faces 84*a* and 84*b* that are closer to the shaft 82. The portion of the file tip 80 between the faces 84*a* and 84*b* is a consistent thickness, because the faces 84*a* and 84*b* are substantially parallel. However, alternatives are contemplated in which the faces 84*a* and 84*b* are non-parallel. The faces 86*a* and 86*b* may be about 1.9 mm long, and the faces 84*a* and 84*b* may be about 5.0 mm long. The working portion 84 may have a width of about 2.5 mm and a length of about 6.9 mm, but these dimensions are not critical. It will be understood that tips may have proportionally larger or smaller surfaces, and surface formations, when such tips are to be used with various living organisms of various sizes.

There is preferably at least one indicium 83 indicating the cutting depth of the file tip 80. This indicium may be about 0.5 mm wide (measured along the longitudinal axis of the file tip 80), and may be formed by any means, including ink or other coloring on the file tip 80, or by grooves extending into, or bands extending out of, the file tip 80. The indicium 83 may be at about 7 mm from the terminal end of the file tip 80. Thus, the depth the file tip 80 extends into a void is indicated by the indicium 83, so the practitioner may determine how deep the file tip 80 extends by where the indicium 83 is located relative to the opening to the void. Of course, more indicia may be placed on the file tip 80 to designate other tip depths.

The file tip 80 is used to file away bone at the opening and in deeper regions of the osteotomy cavity as described below, in order to shape a cavity that receives an implant. The file tip 80 may have an irrigation canal that runs longitudinally therethrough, through which water or another fluid may be pumped to cool the bone during cutting. The irrigation canal may extend from the base 81 to an opening at the distal end of the working portion 84. Fluid may be pumped by the hand-piece through the irrigation canal along the length of the tip 80 and out of the distal end of the working portion 84. A cavitation effect may be caused by the fluid during cutting that may create an improved osteotomy. FIGS. 34-36 show implants with the desired, corresponding osteotomy cavities. Below, Applicant describes the areas where the various file tips described herein may be used to form the outer sidewalls that define the osteotomy cavity.

In general, a cavity is formed during an osteotomy and then an implant (for example, one of the implants shown in FIGS. 34-41) is inserted into the cavity. Surgical protocols for forming the cavity are not described herein in detail, because they are understood by the person having ordinary skill and are well-documented. As a starting step to an osteotomy, one may use an implant radiographic template for a pre-surgical study of each implant site. The implant radiographic template may be used in combination with cross section radiographic images or cone beam computed tomography (CT) scans in order to evaluate the thickness and quality of the residual crestal bone, to evaluate the proper position of the implant site, and to determine the most suitable implant size to be used.

Figure 16:
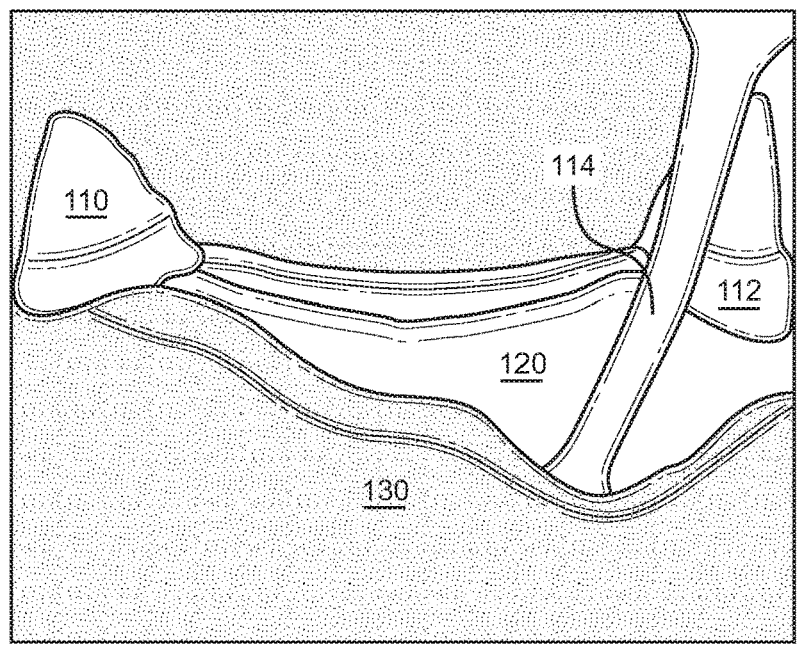
FIG. 16 is a view in perspective illustrating a human mouth undergoing a step of a surgical procedure in which soft tissue is resected from a bone.

Once pre-surgical studies are completed, the site is prepared, such as by resecting the soft tissue, which is shown in FIG. 16, as deemed necessary by the surgeon to expose the implantation site on the bone 120. The soft tissue 130 has been incised along the ridge and around the bases of the teeth 110 and 112 in FIG. 16, and an instrument tip 114 may be inserted between the soft tissue 130 and the bone 120 to separate the soft tissue 130 from the bone 120 farther from the teeth 110 and 112. This instrument may be driven by the piezoelectric surgical device to effectively separate soft tissue from bone. Alternatively, a small incision roughly the size of the planned osteotomy may be created in the soft tissue to allow for minimally invasive surgical treatment.

Figure 17:
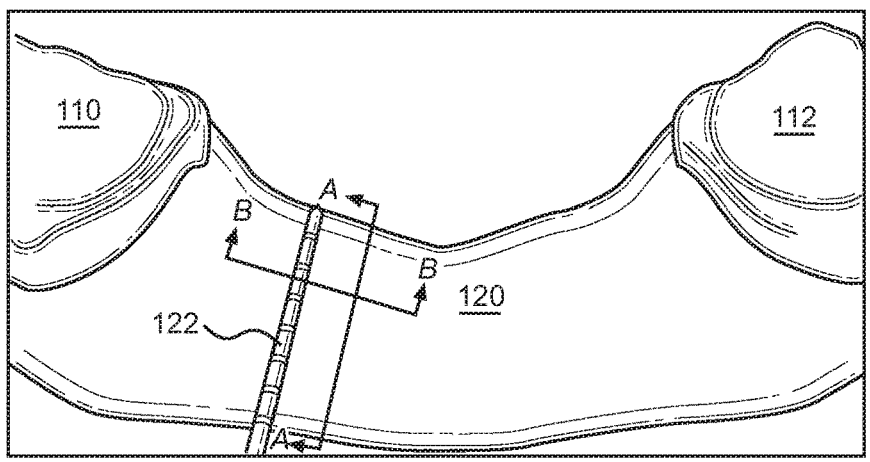
FIG. 17 is a view in perspective illustrating measurement of the thickness of the bone of FIG. 16 after resection of the soft tissue.
Figure 18:
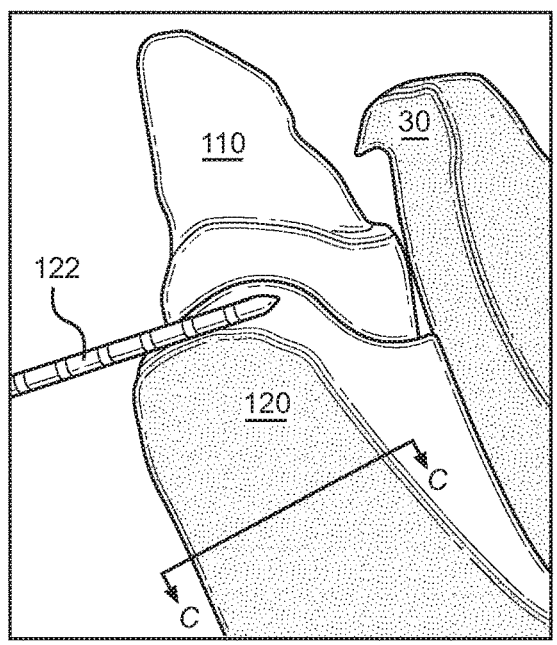
FIG. 18 is a side view in section through the line A-A of FIG. 17 illustrating measurement of the thickness of the bone.

The available ridge thickness may be measured for implant placement during pre-surgical planning by evaluating radiographic images or cone beam CT scans for minimally invasive treatment. Alternatively or additionally, the available ridge thickness may be measured for implant placement, such as by placing a measuring tool 122 across the bone 120 at the site where the cavity will be formed, as shown in FIG. 17. The tool 122 may have markings at every 1.0 millimeter along its length. FIG. 18 shows the tool 122 adjacent the bone 120, where the bone 120 is shown in cross section through the line A-A in FIG. 17. If a human mouth bone ridge is less than about 3.5 mm wide the surgery may be too risky and thus may be halted. However, if the bone ridge is sufficiently large a blade insert of about 1.8 mm (FIGS. 34 and 36) or 2.9 mm (FIG. 35) may be inserted. The person of ordinary skill will understand how to adapt the method and instruments described herein to other anatomical structures, circumstances, and to inserts of various sizes and shapes.

Figure 21:
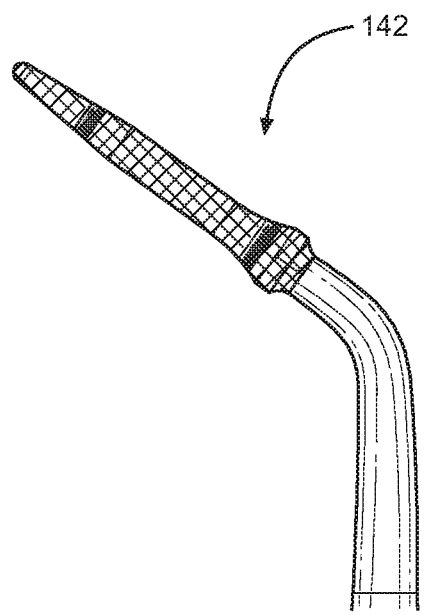
FIG. 21 is a side view illustrating the surgical instrument of FIG. 19.

In a preferred embodiment, initial and reference pilot osteotomies 150, 151 and 152 (FIG. 23), which are described in more detail below, are made using a tip 142 (FIGS. 19 and 21) mounted in the piezoelectric surgical device 140. The tip 142 may have a working portion 144 that is conical and tapered with a length of about 9-12 mm. Circumferential indicia 143 may be formed on the working portion 144 to denote cutting depths, such as at 2.0 and 9.0 mm, which are effectively the distances from the respective indicia 143 to the terminal end of the tip 142. The tip 142 performs initial implant site preparation and bone perforation. The preferably diamond-coated working portion 144 (FIG. 19), which may be about 11.2 mm long with 30 μm grain, may have a conical profile with maximum diameter of 2 mm. The remaining shaft of the tip 142 that connects the working portion 144 to the piezoelectric surgical device 140 may have a titanium nitride (TiN) coating.

Figure 20:
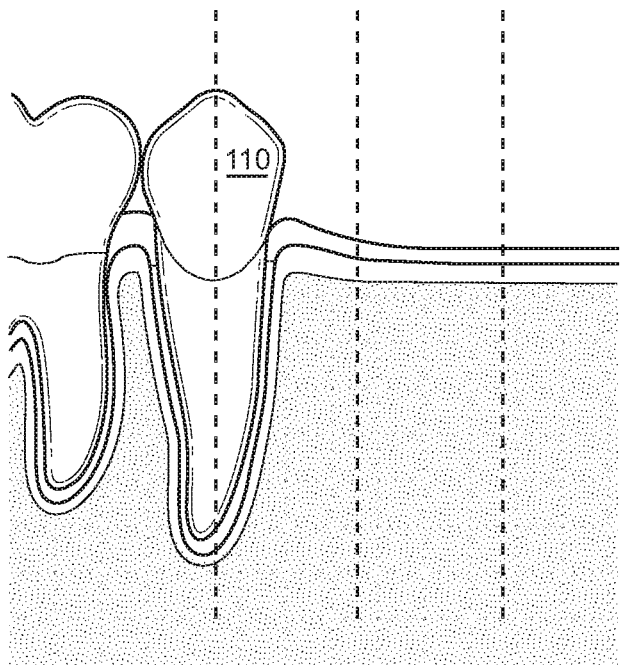
FIG. 20 is a schematic side view in section through the line B-B of FIG. 17 illustrating a bone in which a plurality of teeth is mounted.

Placement of the pilot osteotomy's location using the tip 142 is determined by the practitioner. In the case of partial edentulism (multiple, but not complete, tooth loss), the pilot osteotomy may be created 6-8 mm from the axis of the last single-rooted tooth 110 (see FIG. 20). In the case of mono-edentulism (single tooth loss), the pilot osteotomy may be created 6-8 mm mesio-distally from the proximal teeth that are rooted.

Figure 19:
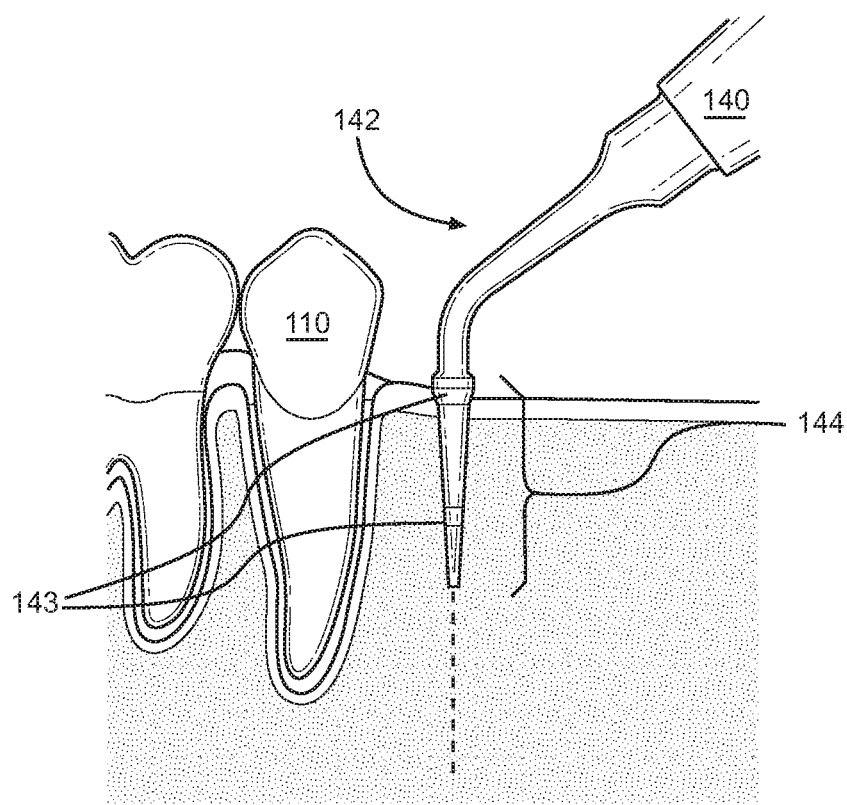
FIG. 19 is a schematic side view in section through the line B-B of FIG. 17 illustrating a step of a surgical procedure in which a surgical instrument cuts into the bone.
Figure 23:
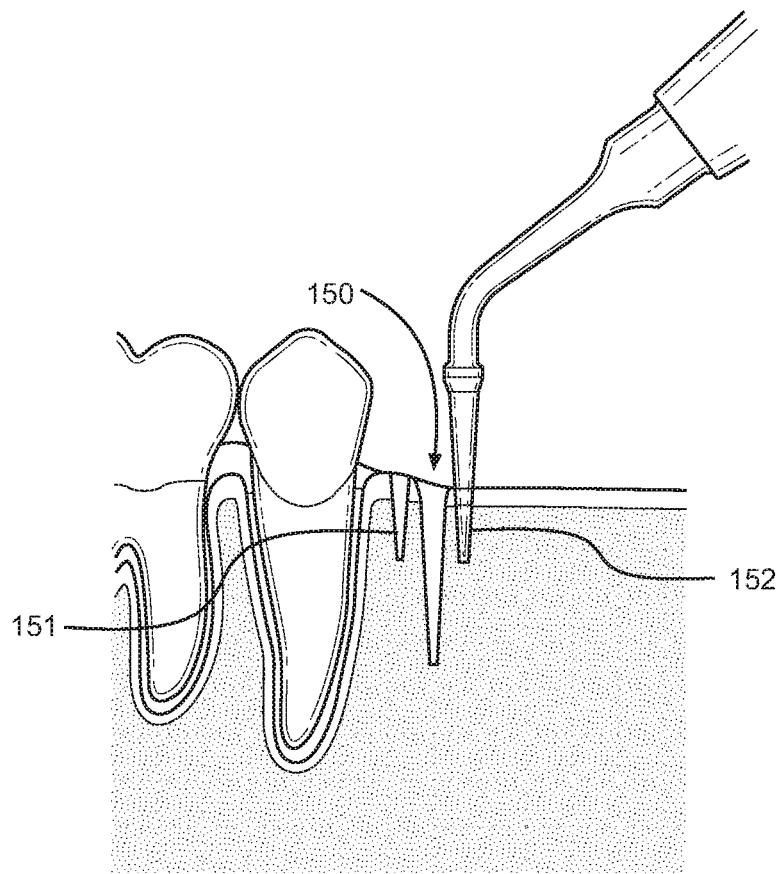
FIG. 23 is schematic side view in section through the line B-B of FIG. 17 illustrating a further step in the surgical procedure in which the instrument of FIG. 21 penetrates the bone.

As is well known with piezoelectric surgical devices, the vibration of an attached tip causes localized micro abrasion of the bone, which is used in a controlled manner by such devices to cut and form a cavity in bone during an osteotomy. The tip 142 is used to create a conically-shaped, pilot void 150 at the center of the desired implant position. The initial pilot void 150 is formed with the tip 142 preferably extended until the larger, upper laser indicium 143 is completely below the upper surface of the bone level, but it is contemplated to insert until the laser indicium 143 is positioned as shown in FIG. 19. The correct depth of the initial pilot void 150, which may be about 9 mm, is ensured when the upper laser indicium 143 extends below the tissue level (as shown in FIG. 19), which is the opening to the void, and then extends slightly further until the top portion of the upper laser indicium 143 falls just below the bone surface. The initial pilot void 150 at the center of the desired implant position preferably leaves about 2 mm between the later-inserted implant and any remaining teeth, as shown in FIG. 23.

Figure 22:
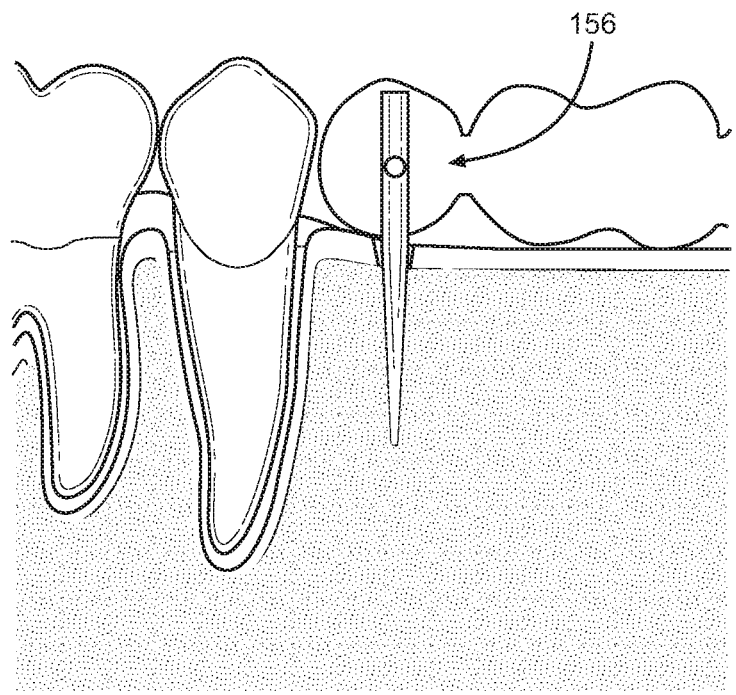
FIG. 22 is a schematic side view in section through the line B-B of FIG. 17 illustrating an alignment pin inserted into a cavity formed in the osteotomy procedure performed using the instrument of FIG. 21.

As shown in FIG. 22, an alignment pin 156 may be used to verify the proper position and angulation of the osteotomy void with the vertical axis of the proximal teeth and to check the distance from the proximal teeth. If the angulation and proximity are as desired, the reference pilot voids 151 and 152 are formed using the tip 142 on each side (mesial and distal) of the initial pilot void 150 at a distance of about 1.0 mm from the closest edge of the initial pilot void 150 and at a depth of about 2.0 mm (using the lower/shallower laser marking 143). Each reference pilot void 151, 152 is considered complete upon reaching the lower, smaller laser marking 143. The total distance between the reference voids 151 and 152 may be about 5 mm.

A micro-saw tip 160 may next be mounted to the piezoelectric device 140 hand-piece to saw a portion of the bone 120, thereby connecting the initial and reference pilot voids 150-152, as shown in FIG. 24. The pilot voids 150-152 define the center and outer edges of the final void into which an implant will be inserted, and the saw 160 is used to cut the bone between the three pilot voids 150-152 to attain the depth and the width, but not necessarily the thickness, of the final osteotomy void. The saw 160 has a flat, rectangular profile with a thickness of about 0.7 mm, which is the thickness of the void formed by the saw, and a width of about 2.2 mm. The saw 160 may have three (or more or fewer) teeth 164 at its terminal, distal end, and these teeth are used for precision cutting. There may be a titanium nitride (TiN) coating on the saw 160, but this may be omitted. The saw tip may not be diamond coated, but such a coating is contemplated. There are laser marks 163 to indicate cutting depths at 9, 11, 13 and 15 mm, but these distances can be modified.

The saw tip 160 is inserted with the center of the terminal end aligned with the pilot void 150, and the reference voids 151 and 152 at the lateral edges thereof. The teeth 164 are forced into the bone until the saw tip 160 reaches the desired depth, as indicated by one of the markings 163, and form a rough void 166 that joins the three pilot voids 150-152. The saw tip 160 may be used to cut laterally further than the reference voids 151 and 152, but this is not typical. The depth of the rough void 166 of FIG. 24 depends on the implant's length, reflected in the markings 163 on the saw tip 160. The depth of the void 166 should not substantially, such as by more than 0.5 mm, exceed the length of the implant to be later inserted into the finished cavity. Similarly, the width and thickness of the void 166 should not substantially exceed the width and thickness of the implant. The cavity should have a size and/or shape that corresponds generally to the size and/or shape of the implant that the finished cavity will receive, although, as explained in some detail below, it is contemplated that the cavity may be smaller in thickness than the implant. For example, a wedge-shaped implant may be inserted into an osteotomy cavity that is deeper than the implant if the shape and/or size of the cavity causes the implant to halt insertion where desired, and be held in place during healing.

A micro-file tip 170 (FIGS. 26-27) is mounted to the piezoelectric device 140 hand-piece and is used to abrade and shape the sidewalls of the rough void 166 to form the more precisely-sized and shaped cavity 176. This is preferably carried out without extending a terminal end of a working portion 174 (FIG. 26) into the cavity so far that the laser marking corresponding to the length (9, 11, 13, 15 mm) of the implant to be inserted into the cavity passes the opening of the cavity. Control over the insertion of the tip 170 limits the depth of the more precisely-sized and shaped cavity 176. The micro-file tip 170 is for micrometric osteotomy, and the diamond-coated working portion 174 may have a flat rectangular profile with a thickness of 0.7 mm, a width of 2.5 mm and a length of 5.0 mm. There may be no titanium nitride (TiN) coating on the working portion 174, but instead there may be a diamond coating of about 120 µm grain. The 0.5 mm laser-cut indicia 173 may indicate depths of 9, 11, 13 and 15 mm, but this may be varied.

Figure 28:
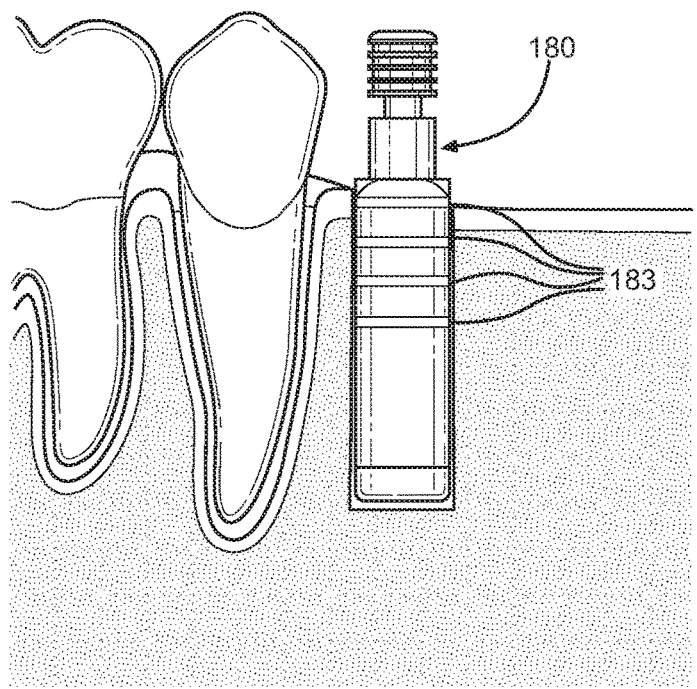
FIG. 28 is a schematic side view in section through the line B-B of FIG. 17 illustrating a fit gauge inserted into the osteotomy cavity of FIG. 26.

Some or all of the dimensions, shape, and alignment of the cavity 176 that are formed with the micro-file tip 170 may be measured or ascertained with the fit gauge 180, which is shown in FIG. 28. The fit gauge 180 simulates the width of a blade implant, and has indicia 183 that correspond to the depth of the osteotomy cavity 176 and correspond to the length of existing implants. However, the fit gauge 180 does not necessarily correspond to the wedge or tapered shape or thickness of any implant. A contemplated fit gauge simulates the shape and/or thickness of an implant, possibly in addition to the depth and width, so that the practitioner does not have to insert the implant into the osteotomy cavity 176 in order to determine whether the cavity is the correct size and shape. The preferred fit gauge 180 permits the practitioner to determine whether the depth and width of the cavity are correct prior to further modifying the shape and thickness of the cavity. Thus, the fit gauge 180 may be inserted to the laser mark 183 that corresponds to the length of the implant to be inserted, even before thickness trimming of the cavity 176 occurs as described below.

As shown in FIG. 28, and in a contemplated example, the top indicium 183 is at the opening of the cavity, indicating that the depth of the cavity is about 9 mm. If the fit gauge 180 does not fit within the cavity to the depth desired, either or both of the prior steps using the micro-saw tip 160 and the micro-file tip 170 may be repeated until the desired width and length (depth) are achieved.

Once the desired length and width of the cavity 176 are achieved, the shape of the cavity 176 is similar to that of the finished cavity into which an implant is inserted, except possibly in the thickness direction. The thickness of the cavity 176 may be substantially the same from the opening end to the apical (deepest) end, or it may vary along the length. However, because the implants that are subsequently inserted into the cavity may have a wedge-shape that tapers from the thickest end (the end nearest the opening) to the thinnest end (the end deepest in the cavity), in some embodiments the cavity 176 may be further shaped in order to give the cavity a tapered shape. This further shaping may include the step of inserting a working portion of a tip into the cavity 176 and seating abrasive surfaces of the tip against the cavity sidewalls to abrade the sidewalls and increase the cavity's thickness in selected places along the cavity sidewalls. This further shaping may be to taper the sidewalls gradually from the opening end toward the apical end, or to taper the sidewalls at a more extreme angle in one or more locations along the length of the cavity 176, or a combination.

After the lateral (width) and depth (length) dimensions of the cavity 176 are of the desired shape and size to cooperate with an implant that will subsequently be inserted therein, it is desirable to shape and size the cavity mesio-distally, which is in the direction perpendicular to the plane of the illustration of FIG. 29, in the crestal bone. This is referred to herein as the thickness of the cavity. This shaping and sizing may be accomplished with a file tip 190 (FIG. 29) mounted to the piezoelectric device 140 hand-piece. In one embodiment, the file tip 190 is substantially identical to the file tip 40 shown and described above in relation to FIGS. 1-5. In other embodiments, the file tip 190 may differ from the file tip 40.

The file tip 190 is mounted to the hand-piece and vibrated at a conventional frequency, and the surgeon inserts the file tip 190 into the cavity. The file tip 190 desirably has a greater thickness than the cavity, and therefore the insertion causes the opposing faces of the file tip 190, which may be equivalent to the faces 44a, 44b, 46a and 46b of the file tip 40, to seat against the sidewalls of the bone 120. If the faces of the tip 190 are equivalent to the faces 44a, 44b, 46a and 46b of the file tip 40, these equivalent faces abrade the sidewalls and increase the thickness of the cavity where contact is made. Preferably contact is made along the entire width of the cavity and to a desired depth until the thickness of the cavity is consistent along the entire cavity width, and consistent or taped to the desired depth. If the tip 190 is not as wide as the cavity 176, then the working portion may be moved along the entire width of the cavity by the practitioner until the desired shape is completed.

Figure 29:
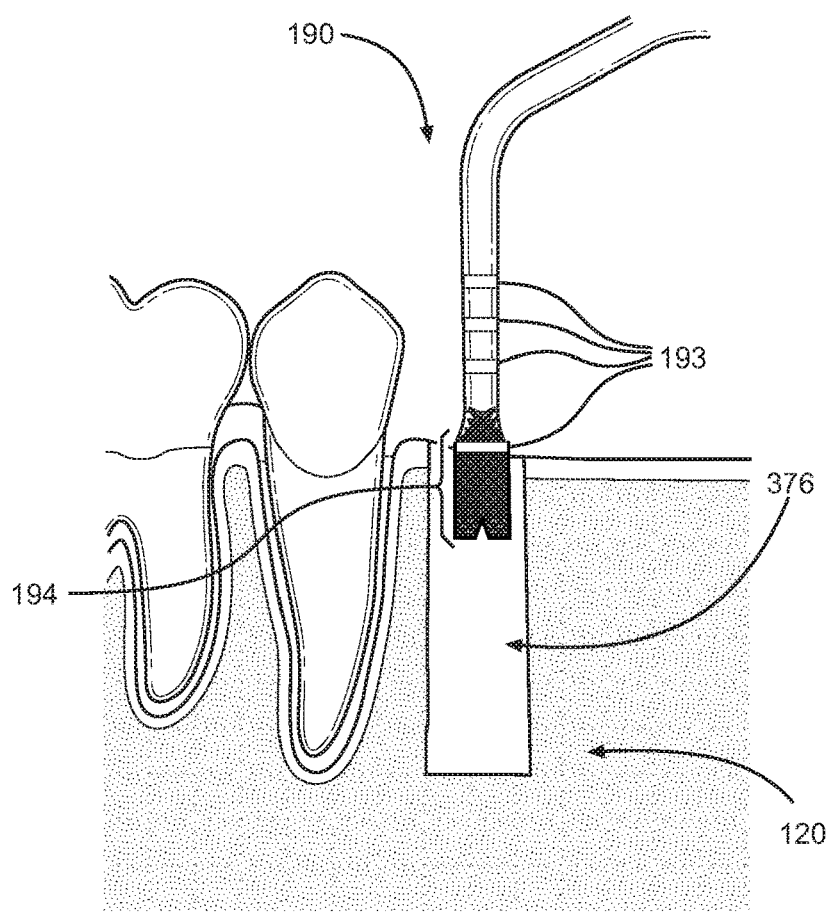
FIG. 29 is a schematic side view in section through the line B-B of FIG. 17 illustrating a first file tip inserted into the cavity to modify the thickness thereof.

If a 1.8 mm thick implant is to be inserted into the cavity 176, for most circumstances the depth the file tip 190 may be inserted into the cavity should not exceed the laser mark 193 at the base of the working portion 194 (3.0 mm deep), which is shown in position in FIG. 29. If the bone is sclerotic, however, or other circumstances exist, as determined by the surgeon, the depth of the insertion of the tip 190 may be increased to the depth of the other laser marks 193 corresponding to the 11.0, 13.0 and 15.0 mm implant lengths, or any length in between. This insertion will thereby shape the sidewalls of the cavity to the corresponding depth. For the 1.8 mm implant 210 shown in FIG. 34, the shape of the sidewalls adjacent the opening of the cavity will typically be that shown and described below in association with FIG. 34, including sidewalls 202-205.

There are other depth laser marks 193 on the tip 190, and the surgeon may optionally insert until the tip 190 reaches the next mark 193, some other mark 193 or adjacent a mark 193, and thereby extend the depth to which the tip 190 extends to abrade the sidewalls of the cavity. The surgeon may thereby further extend what is shown as the "necked-down" region at the sidewalls 204 and 205 in FIG. 34 from about 3.5 mm from the opening of the cavity to 4.5, 5.5, 8.5, 10.5, 13.0 mm or any other depth desired. The surgeon does so by extending the depth that the terminal end, which corresponds to the faces of the tip 190 that are equivalent to the faces 46a and 46b on the tip 40, reaches. Thus, if the tip 190 is extended farther than is shown in FIG. 34, the sidewalls 204 and 205 extend correspondingly farther toward the apical end than is shown in FIG. 34.

FIG. 34 is a view in section through the bone 120 along the line A-A of FIG. 17, and shows the osteotomy cavity sidewalls 376 (made up of reference numerals 200 to 205) and the 1.8 mm thick implant 210. The sidewalls 200 and 201 may be formed with the micro-saw 160 and the micro-file 170 as described above. The sidewalls 202 and 203 may be formed with the file tip 190 when the file tip 190 is inserted until the shallowest laser mark 193 reaches the top of the bone 120 at the opening of the finished cavity 376, as shown in FIG. 29. The terminal end faces of the file tip 190 that are equivalent to the faces 46a and 46b of the file tip 40 form the sidewalls 204 and 205 when the file tip 190 is inserted until the first (shallowest) laser marking 193 is at the opening of the osteotomy as in FIG. 29. The file tip 190 may be inserted beyond the position shown by the sidewalls 204 and 205, but the position of the sidewalls 204 and 205 is typical for the 1.8 mm insert 210 in healthy bone.

Figure 37:
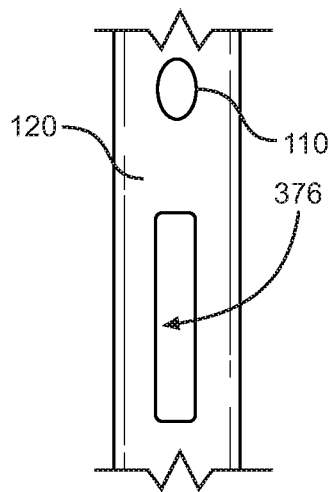
FIG. 37 is a top view in section through the line C-C of FIG. 18 illustrating the shape of the void when viewed in section along a plane extending perpendicular to the longitudinal axis of the void 376.

The cavity 176, which is modified to form the final cavity 376 by the process described herein, has a substantially rectangular shape when viewed in section through a plane that contains the initial and reference pilot voids 150-152, which view is through the line B-B of FIG. 17 and shown in FIGS. 26 and 28-33. The shape of the cavity 376 when viewed in section along a plane extending perpendicular to the longitudinal axis of the cavity 376 is shown in FIG. 37, and this is shown through the line C-C of FIG. 18. The shape of the cavity is substantially non-circular, and preferably rectangular, which may include rectangular with slightly rounded corners. FIGS. 34-36 are views in cross section through a plane along the line A-A (FIG. 17), which plane is perpendicular to the section plane of FIGS. 26 and 28-33, and show the final cavity 376 tapered and with at least one region where the cavity in the coronal region (near the opening) "necks down" to a smaller thickness gap in the apical region. The sidewalls 204 and 205 define the necked-down region of one embodiment where the cavity tapers from the thickness between the sidewalls 202 and 203 to the thickness between the sidewalls 200 and 201.

The "necked down" region is a segment of the length of the cavity in which there is a per unit length change in the cavity thickness greater than the per unit length change in the cavity thickness along the entire cavity length. That is, along the length of the necked-down portion, which may be about 0.5 mm in FIG. 34, the change in thickness along that 0.5 mm of cavity length exceeds the change in cavity thickness along the length of the entire cavity, which may be 9 mm. This is visible in the necked-down region found between the sidewalls 204 and 205 of FIG. 34.

The shape and relative thickness of the final cavity 376 cooperates with the shape and size of the implant 210. The width of the final cavity 376 is substantially equal to the width of the implant 210, and the length of the final cavity 376 and the length of the implant 210 may be substantially equal, although the cavity length may exceed the implant length slightly. The cavity 376 and the implant 210 preferably differ in thickness, typically by the cavity's thickness being smaller than the implant's thickness. For example, at the coronal region near the opening, where the denser, cortical bone 120 is typically found, the cavity 376 may be about 1.6 mm thick while the implant's main wall is 1.8 mm thick and the sagittal fins that protrude from the opposing surfaces of the main walls are 2.0 mm apart at their tips. The thickness difference is smaller at the coronal region near the opening than in the trabecular (cancellous) region that is closer to the apical end near the center of the bone where the bone is porous. In the trabecular region the difference in thickness between the cavity and the implant can be greater, and the cavity may be substantially thinner than the implant. It is desirable, for the sake of initial retention of the implant 210, to create a cavity that has a thickness smaller than the implant along the entire cavity length, but there may be segments where that is not so, such as in the most apical end, as shown in FIG. 34. Furthermore, it is preferred that the difference in thickness be greater where there is porous, trabecular bone, because such porous bone may be more greatly deformed than the denser, cortical bone without harm by the implant as the implant forces the cavity sidewalls outward during insertion. Rather than harming the patient, damage to the bone tissue can induce a remodeling response that is beneficial to the healing process, and this is an advantage that the invention provides.

Thus, the general shape of the cavity is tapered from a greater thickness at the opening, cortical end to a smaller thickness at the deeper, apical end and the cavity is typically thinner than the implant, at least at points along the cavity. In one embodiment, the cavity is thicker at any given position that is closer to the opening end than any other position closer to the apical end. This results from a gradual reduction in thickness of the cavity from opening end to the opposite end. However, such a gradual reduction is not critical. Indeed, the sidewalls of the cavity may be parallel for a substantial portion of its length from opening end to apical end with sudden reductions in thickness along small lengths of the cavity, which are the "necked-down" regions. Alternatively, the sidewalls may gradually taper with sudden reductions in thickness. Nevertheless, with both examples, there is an overall reduction in thickness from the opening end to the apical end.

It is contemplated to form localized portions of the cavity's length in which a substantial reduction in thickness is achieved over a given unit of length of the cavity. For example, a cavity may change in thickness by a total of about one millimeter over the length of an entire 10 mm long cavity. However, in one cavity this may happen gradually at about 0.1 mm of thickness per 1.0 mm of length. In another cavity, the reduction in thickness may happen mostly or even entirely in a middle, necked-down portion that extends only 1.0 mm of the length of the cavity. At all other portions of the length, the sidewalls are substantially parallel. More typical is a gradual reduction in thickness with one, two or more necked-down portions at spaced intervals. Any combination of these examples is contemplated, and the "necked-down" portions are where large changes in thickness occur for a unit of length of the cavity.

As an example, two 10.0 mm long cavities may have a difference in thickness of 1.0 mm between their opening ends and apical ends. Both cavities thus have a per unit length thickness change of 0.1, which is 0.1 mm for every 1.0 mm of cavity length. Nevertheless, the first cavity may have a gradually changing thickness along its entire length and no necked-down regions. The second cavity may have substantially parallel or slightly tapering sidewalls along about 8.0 mm of its length, and in two, 1.0 mm long segments the thickness may be reduced by 0.5 mm each. In the second example cavity, each 1.0 mm long segment meets the requirement of being "necked-down" because the change in thickness per unit length for each 1.0 mm long segment (0.5/1.0=0.5) is substantially greater than the change of thickness per unit length of the entire cavity (1.0/10.0=0.1).

The sidewalls of the cavity 376 at the wider portion of the necked-down region formed by the sidewalls 204 and 205 may have a thickness difference with the sidewalls 200 and 201 from the earlier cavity 176 of about 100%, 150% or more. At the cortical bone, the difference in thickness may be about 10% of the thickness of the cavity. In FIG. 34, the sidewalls 204 and 205 may be formed by the angled faces at the terminal end of the file tip 190 abrading the sidewalls defining the cavity 176 to form the cavity 376. If the file tip 190 is forced farther into the cavity 176, the position of the sidewalls 204 and 205 is moved closer to the apical end of the cavity, which results in a smaller thickness difference between the exterior surface of the implant 210 and the sidewalls of the cavity. This results in less of a "press fit" of the implant 210 in the cavity. A smaller press fit in some regions may be desired under some circumstances, and the surgeon will determine exactly how far to insert the file tip 190 into the cavity 176 to achieve the desired press fit in the final cavity 376.

The position of the necked-down region closest to the opening, which is the coronal ends of the sidewalls 204 and 205, may be varied. The coronal end of the necked-down portion can be as close as about 0.5 mm from the opening end of the cavity to as far as within 1.0 mm of the deepest region of the cavity.

The first 3 mm of the implant 210 shown in FIG. 34 preferably has a thickness of about 1.8 mm from main wall to main wall. The thickness from the extreme tip of the sagittal fin 206 to the opposing sagittal fin tip 207 is 2.0 mm at the opening, and decreases lower (apically) on the implant 210. The thickness at the apical tip of the implant is about 0.5 mm for current implants, whereas newer implant designs may have slightly thicker tips, such as about 0.54-0.57 mm.

The general shape of the final cavity 376 in the view of FIG. 34 includes a larger thickness in the coronal region near the opening and a necked-down portion that transitions to a smaller thickness in the apical region farthest from the opening. The exact size of the cavity 376 in particular regions may vary due to the conditions of the patient's bone and other factors, so that the exact size and shape of the cavity may be varied by the surgeon to fit the circumstances. The thicker portion near the cortical region that tapers to the apical region cooperates with the implant as described herein and as will be apparent to the person of ordinary skill from the description herein.

During formation of the cavity, the pilot voids are formed and then the micro-saw and micro-file are inserted until they form the sidewalls 200 and 201 on both sides of the cavity from the extreme cortical region to the extreme apical region. Then the file tip 190 is inserted until it forms the sidewalls 202, 203, 204 and 205 along the entire width of the cavity. The cavity 376 formed with this series of bone-shaping tools has a thickness difference in the coronal region, which is at the opening of the cavity, of about 0.2 mm at the body (main walls) of the implant, and about 0.4 mm at the tips of the sagittal fins 206 and 207. This thickness difference causes a "press fit" in which the bone is compressed and/or cut by the sagittal fins 206, 207 and the body of the implant during insertion so that, upon full insertion, the implant 210 has a tight, friction-fit with the sidewalls of the bone 120 defining the cavity 376. This press fit is small at the opening where the more dense cortical bone is found, and increases substantially where the spongy, trabecular bone is found, such as at the necked-down portion where the cavity sidewalls 204 and 205 are formed. At the cavity sidewalls 204 and 205, there is a substantial press fit of the spongy, trabecular bone, and this substantial press fit holds the implant in position until the bone can grow into and around the implant over time. The existence of at least one necked-down region that transitions from the thicker cavity at the opening to the thinner cavity at the apical end, may be found in the cavities created under the present invention.

The initial steps, such as the micro-saw and micro-file forming sidewalls that reach the deepest region of the osteotomy and form the width of the cavity, apply to all implants. Furthermore, the file tip 190 is also used, to the degree desired by the surgeon, in the formation of essentially all cavities. The following steps are optional, depending upon the shape and size of the implant and the medical circumstances, as determined by the practitioner. These steps are typically followed if a 2.9 mm thick implant 310 shown in FIG. 35 is to be inserted into the cavity 476. The practitioner may insert the file tip 190 until its extreme tip reaches a depth of about 9.0 mm as shown in FIG. 35 by the sidewalls 304 and 305, which are created by the terminal end faces of the tip 190, which are equivalent to the faces 46a and 46b on the tip 40. This depth is contemplated to be about 12.5 mm in some embodiments. The sidewalls 304 and 305 neck down and correspond with the sidewalls 204 and 205 of FIG. 34, but extend deeper than the sidewalls 204 and 205 of FIG. 34, possibly due to the overall size difference of the implant 310 as compared to the implant 210. The conditions of the patient's anatomy, as well as the size and insertion distance of the implant, may affect how far the necked-down region, or regions, of the cavity extend.

The deepest necked-down region, which is formed by the file tip 190, may be extended farther than shown in FIG. 35, but also may be extended to a smaller depth, for example if more or less of a press fit is desired near the deepest necked down region. The surgeon may enlarge the final cavity 476 with the file tip 190 to the desired cavity depth as indicated by the laser markings 193 corresponding to the length (e.g., 9.0, 11.0, 13.0, 15.0 mm) of the implant to be used. Of course, other laser marking insertion lengths are contemplated, including 3.0, 4.0, 5.0, 6.0, 7.0, 8.0, 10.0, 12.0, 14.0, and 16 mm depths.

Figure 30:
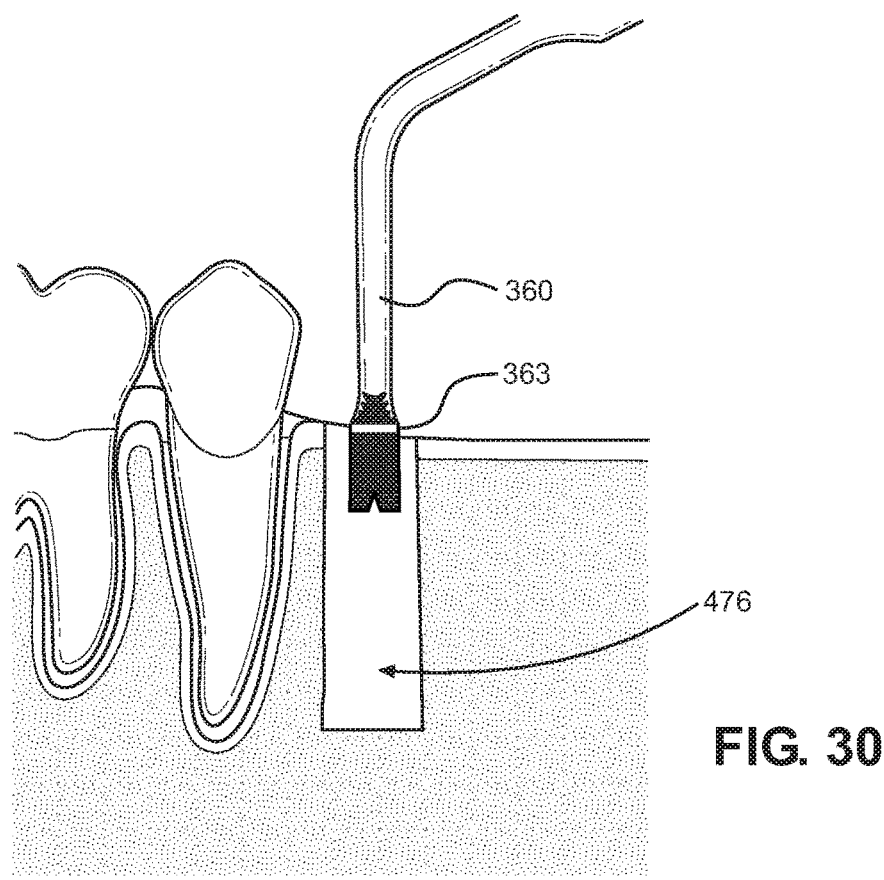
FIG. 30 is a schematic side view in section through the line B-B of FIG. 17 illustrating a second file tip inserted into the cavity to modify the thickness thereof.
Figure 31:
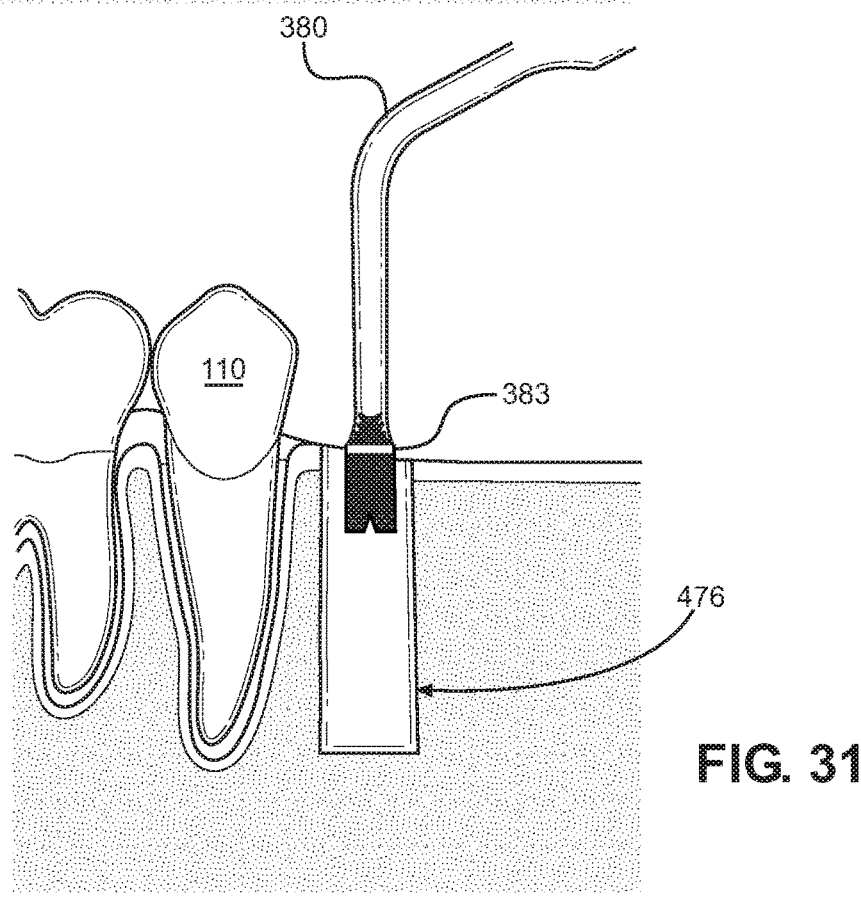
FIG. 31 is a schematic side view in section through the line B-B of FIG. 17 illustrating a third file tip inserted into the cavity to modify the thickness thereof.
Figure 32:
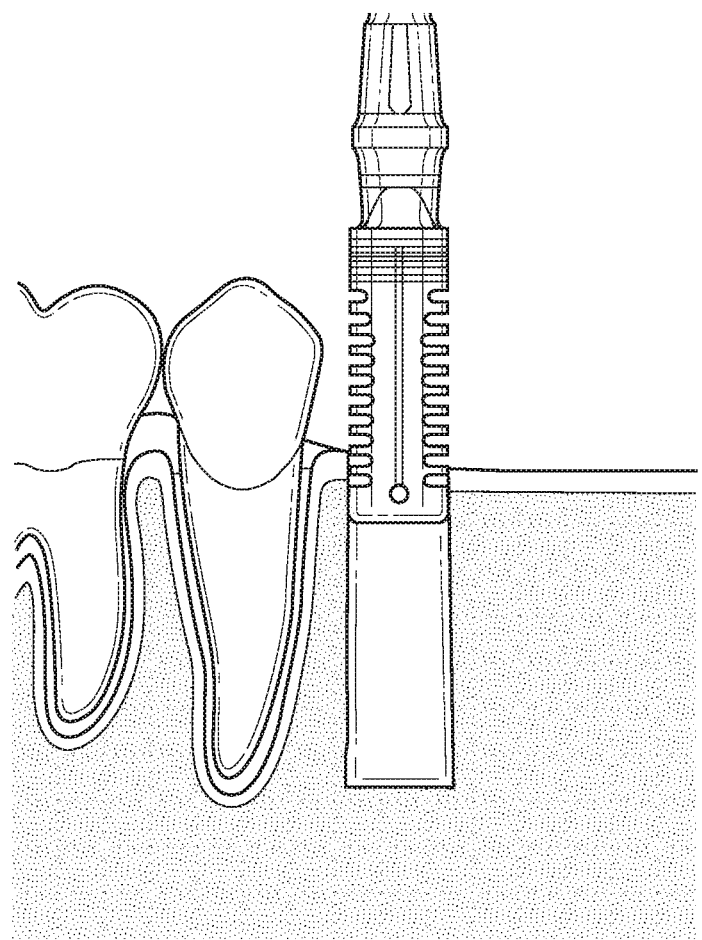
FIG. 32 is a schematic side view in section through the line B-B of FIG. 17 illustrating insertion of an implant into the cavity.
Figure 33:
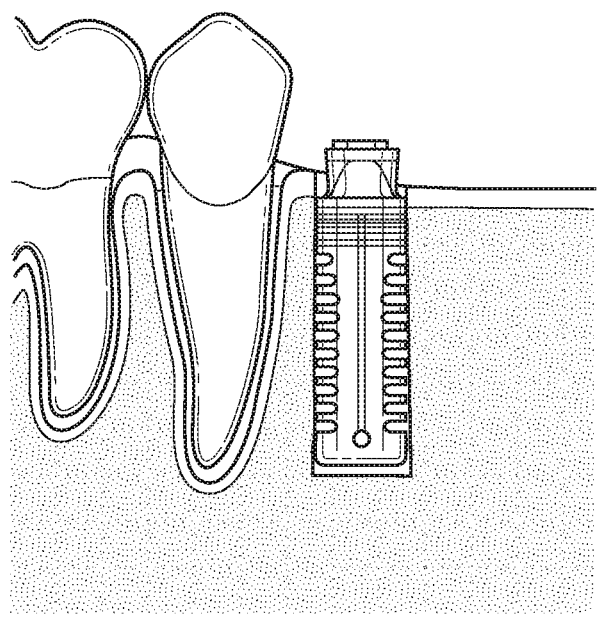
FIG. 33 is a schematic side view in section through the line B-B of FIG. 17 illustrating the implant of FIG. 32 fully inserted into the cavity.

Alternatively, or additionally, the cavity 476 may be enlarged by the file tips 360 and/or 380, which are shown in FIGS. 30 and 31 and may be equivalent to the file tips 60 and 80, respectively, described above and shown in FIGS. 6-15. FIG. 35 shows insertion of an implant 310 that is 2.9 mm thick, which is about 1.1 mm thicker than the implant 210 of FIG. 34. When a 2.9 mm thick implant is to be placed in a cavity, the more precisely-sized and shaped cavity 176 may be formed, or the cavity 376 may be formed. In either case, additional mesiodistal space may be created by abrading the sidewalls as determined by pre-surgical planning. Thus, the practitioner may attach the wedge-shaped file tip 360 to the hand-piece and continue to enlarge the cavity 376 mesiodistally to the desired thickness at the desired positions along the cavity length, thereby forming the final cavity 476. Alternatively, the practitioner may extend the tip 190 further than in the cavity 376 to form the sidewalls 304 and 305, and thus a necked-down portion, about 8.0 mm from the opening. The surgeon may then attach the file tip 360 to the hand-piece, actuate the hand-piece in a conventional manner to vibrate, and then insert the terminal end of the file tip 360 into the cavity to its depth marking 363 as shown in FIG. 30 all along the entire width of the cavity to form the cavity 476 shown in FIG. 35. This causes the terminal end faces of the tip 360 to form the sidewalls 366a and 366b at the desired depth in the cavity, which may be about 5.0 mm from the opening (at the opening ends of the sidewalls), and the sidewalls 364a and 364b that are slightly thicker (about 2.3 mm) than the sidewalls previously formed by the tip 190 (about 1.4 to 1.6 mm). Depending on the amount of bone mineralization at the implant site, this step may not be necessary. However, failure to provide proper mesiodistal space in the cavity may increase the risk of iatrogenic bone fracture, as will be understood by the person of ordinary skill.

The sidewalls of the osteotomy 476 that correspond to the faces of the file tip 360 are the sidewalls 364a and 364b, which are formed by the faces of the file tip 360 that are equivalent to the sidewalls 64a and 64b of the tip 60 described above. The sidewalls 366a and 366b are formed by the faces of the file tip 360 that are equivalent to the sidewalls 66a and 66b of the tip 60 described above. Of course, the file tip 360 may be inserted more or less than the depth that the sidewalls 364a, 364b, 366a and 366b are shown extending in FIG. 35, and this will be determined by the surgeon. If the tip 360 is the last tip inserted into the cavity 476, there is a second necked down region formed by the sidewalls 366a and 366b.

The surgeon may attach to the hand-piece and then insert the file tip 380 into the cavity 476 as shown in FIG. 31. The sidewalls of the cavity that correspond to the faces of the file tip 380 are the sidewalls 384a and 384b, which are formed by the faces of the file tip 380 that are equivalent to the sidewalls 84a and 84b of the tip 80 described above. The sidewalls 386a and 386b are formed by the faces of the file tip 380 that are equivalent to the sidewalls 86a and 86b of the tip 80 described above. Of course, the file tip 380 may be inserted more or less than the depth that the sidewalls 384a, 384b, 386a and 386b are shown extending in FIG. 35. If the tip 360 is the last tip inserted into the cavity 476, there is a second necked down region formed by the sidewalls 386a and 386b that are slightly farther apart than the sidewalls 366a and 366b that were previously formed.

The file tips 360 and 380 may have respective maximum thicknesses of 2.3 mm and 2.7 mm, and these tips 360 and 380 may be used as described above to make the osteotomy 376 thicker, typically for the 2.9 mm thick implant 310. Other tip thicknesses are contemplated, such as 2.8 mm and 2.9 mm. The 2.9 mm thick tip may be for patients with very dense bone. In these patients, the fin and apical press fit provide initial primary implant stability. The bone sidewalls may shrink slightly during the initial 24 hours after surgery due to the tissue's viscoelastic material properties, thereby providing additional stability.

The file tips 360 and 380 form necked-down portions, which may be defined by the sidewalls 366a and 366b or the sidewalls 386a and 386b. The file tips 360 and 380 may be inserted into the cavities 376 or 476 more or less than shown in FIGS. 34 and 35, thereby moving the necked-down portion accordingly from those shown. In the embodiment of FIG. 35, there are two necked-down portions, one formed by the sidewalls 304 and 305, and one formed by the sidewalls 386a and 386b (or alternatively the sidewalls 366a and 366b). It is also contemplated to have three, four, five or more necked down portions, each made by progressively larger file tips similar to the tips 190, 360 and 380, each of which is inserted a smaller distance into the cavity made by the micro-saw and the micro-file.

The file tips 360 and 380 may have parallel or non-parallel opposing faces, and these tips 360 and 380 may form a cavity that is thicker from the opening to the shallowest necked-down point than the file tip 190, or may have no taper along the sidewalls 364a, 364b and 384a and 384b. Thus, from the opening of the cavity to the shallowest necked-down portion, there may be no tapering in thickness if the tips 360 and/or 380 are used. However, in the region of the cavity 476 where the file tip 190 is used, the sidewalls formed, which may be the sidewalls 302 and 303, taper slightly toward the necked-down region defined by the sidewalls 304 and 305, due to the tapering in the faces of the file tip 190.

When a 2.9 mm implant 310 that is shown in the final cavity 476 of FIG. 35 is to be inserted, the surgeon may first use the micro-saw and micro-file to form the thin, deep portion of the cavity 476 defined by the sidewalls 300 and 301, then uses the file tip 190 to form the sidewalls 302, 303, 304 and 305 of the cavity 476 (shown to a depth of 9 mm).

Of course, the depth that the file tip 190 extends may be varied based on the implant and the patient's anatomy and tissue conditions. The tip 360 may then be used to form the sidewalls 364*a*, 364*b*, 366*a* and 366*b*, and then, optionally, the tip 380 may be used to form the sidewalls 384*a*, 384*b*, 386*a* and 386*b*. The tip 360 may be used to enlarge the cavity from the thickness caused by the tip 190, or the tip 380 may be used subsequently to the file tip 190, thereby skipping any use of the tip 360. A surgeon may not use the file tip 380 if a press fit at the cortical and trabecular regions is desired. The press fit in the trabecular region is affected more by the depth that the file tips 190, 360 and 380 are inserted than the thickness of these tips.

Typically, positioning the necked-down portion closest to the opening of the cavity corresponds with the first large indicium/mark in the implant aligned with the cavity opening, but this is not required. It is contemplated that the necked-down portion closest to the opening may correspond to aligning the second or third indicium/mark of the implant at the cavity opening.

The sagittal fins 206, 207 and 306, 307 may reduce the friction between the implant and the bone during insertion. This may be due to focusing the surface-to-surface sliding to where the fins contact the bone on both sides.

The first 3.3 mm of the implant 310 may have a thickness of 2.9 mm, without considering the sagittal fins 306 and 307, in order to facilitate insertion into a 2.7 mm thick cavity. The thickness between the sagittal fins 306 and 307 may be 3.1 mm. The thickness of the implant 310 at the apical tip may be 0.5 mm, and this inserts into the apical portion of the cavity formed by the saw and micro-file that is about 0.7 mm thick.

Once the desired cavity is formed, the implant is inserted in the surgical site. This can be performed manually or by using additional equipment, which may be an implant placement device that uses low or high frequency, longitudinal impacts to drive the implant into the cavity. Additional implants are placed as necessary by repeating the process described above and shown. After completion, the soft tissue is sutured around a cover screw that may be placed on the implants. A splint that secures the posts to each other may also be used.

The term "press fit" as used herein means the amount of interference between the implant and the bone to prevent the implant from moving relative to the bone. Interference is caused by many factors, including the differences in geometry and the forces holding the structures together.

It is contemplated that the surgeon may choose to vary the depth where the necked-down portion is located from the depth shown and described herein. Two examples of depths for the necked-down region with the 1.8 mm implant 210 are where it is drawn in FIG. 34 and all the way at the bottom of the cavity 376. Of course, the necked-down region may be anywhere between these two extremes, or even closer to the opening than shown in FIG. 34. The most preferred depth for the necked-down portion when using the implant 210 is about 3.5 mm from the opening as shown in FIG. 34. When using the implant 310, the most preferred depth for the transition of the lowest necked-down portion is about 8.0 mm, as shown in FIG. 35, and about 5.0 mm for the upper necked down portion. The smallest depth contemplated for the least apical end of the necked-down portion is about 0.7 mm, and more preferably about 2.0 mm. The depth could vary between about 0.5 mm and about 15 mm.

In general, it is desirable to have interference in the cortical bone of 0.0 to 0.5 mm total interference for the implants described herein, or a thickness difference of about 0 to about 10% of the total thickness of the implant. It is preferred to have a 5-7% difference for cortical bone. In the trabecular bone, it is desirable to have 0.0 to 1.5 mm total interference for the implants described herein, which is a thickness difference of about 0 to about 150% of total thickness of the implant. When there is a difference of 0.0, this is when the implant just contacts the bone without any difference in thickness between the two.

Figure 38:
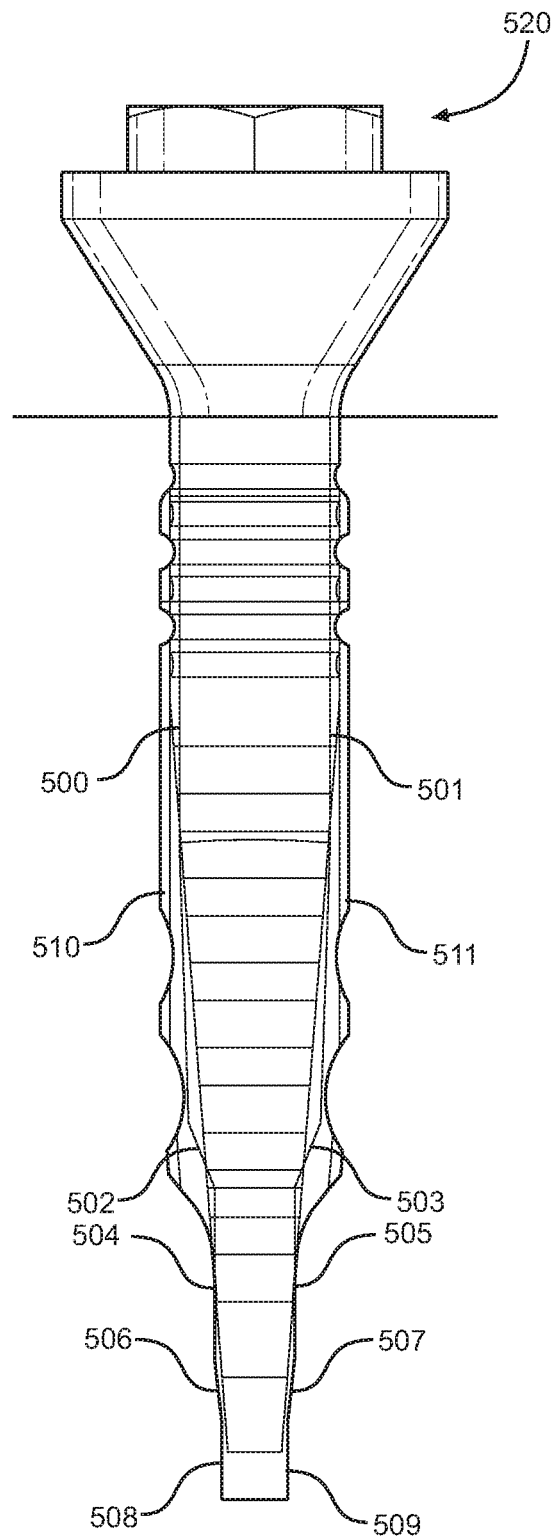
FIG. 38 is a side view in section illustrating an implant inserted into a cavity.

FIG. 38 is a view in section through the bone 120 along the line A-A of FIG. 17, and shows the osteotomy cavity sidewalls 376 (made up of reference numerals 500 to 509) and the implant 520. The sidewalls 508 and 509 may be formed with the micro-saw 160 as described above. The sidewalls 504, 505, 506, and 507 may be formed with a micro file 170 as described above. The sidewalls 500 and 501 may be formed with the file tip 190 when the file tip 190 is inserted until the second laser mark 193 reaches the top of the bone 120 at the opening of the cavity 376, as shown in FIG. 29. The terminal end faces of the file tip 190 that are equivalent to the faces 46*a* and 46*b* of the file tip 40 form the sidewalls 502 and 503 when the file tip 190 is inserted until the second laser marking 193 is at the opening of the osteotomy. The file tip 190 may be inserted beyond the position shown by the sidewalls 502 and 503, but the position of the sidewalls 502 and 503 is typical for the insert 520 in sclerotic bone.

FIGS. 38-41 are views in cross section through a plane along the line A-A (FIG. 17), which plane is perpendicular to the section plane of FIGS. 26 and 28-33, and show the final cavity 376 tapered and with at least one region where the cavity in the coronal region (near the opening) "necks down" to a smaller thickness gap in the apical region. The sidewalls 502 and 503 define the necked-down region of one embodiment where the cavity tapers from the thickness between the sidewalls 500 and 501 to the thickness between the sidewalls 504 and 505.

During formation of the cavity, the pilot voids are formed and then the micro-saw is inserted until it forms the sidewalls 508 and 509 on both sides of the cavity from the extreme cortical region to the extreme apical region. Then the micro file tip 170 is inserted until it forms the sidewalls 504, 505, 506 and 507 from the extreme cortical region to the extreme apical region. The micro file tip 170 insert cuts to the same depth as the micro-saw, but the tapered tip of the micro file tip 170 does not file the sidewall all the way to the extreme apical end of the cavity. Next the file tip 190 is inserted until it forms the sidewalls 500, 501, 502 and 503 along the entire width of the cavity. The cavity 376 formed with this series of bone-shaping tools has a thickness difference in the coronal region, which is at the opening of the cavity, of about 0.2 mm at the body (main walls) of the implant, and about 0.4 mm at the tips of the sagittal fins 510 and 511. This thickness difference causes a "press fit" as described above. The existence of at least one necked-down region that transitions from the thicker cavity at the opening to the thinner cavity at the apical end, may be found in the cavities created under the present invention. The press fit deeper than the necked-down region is about 0.15 mm at the implant and 0.75 mm at the sagittal fin (see FIG. 38).

The micro-file 170 may have a tapered tip due to shaping of the metal substrate, the varying thickness of an abrasive coating, or any other reason. This may cause the formation of a tapering in the cavity as defined by two sidewalls 506 and 507 adjacent the apical end of the original sidewalls 508 and 509. Insertion of the implant 520 is as described herein.

Figure 39:
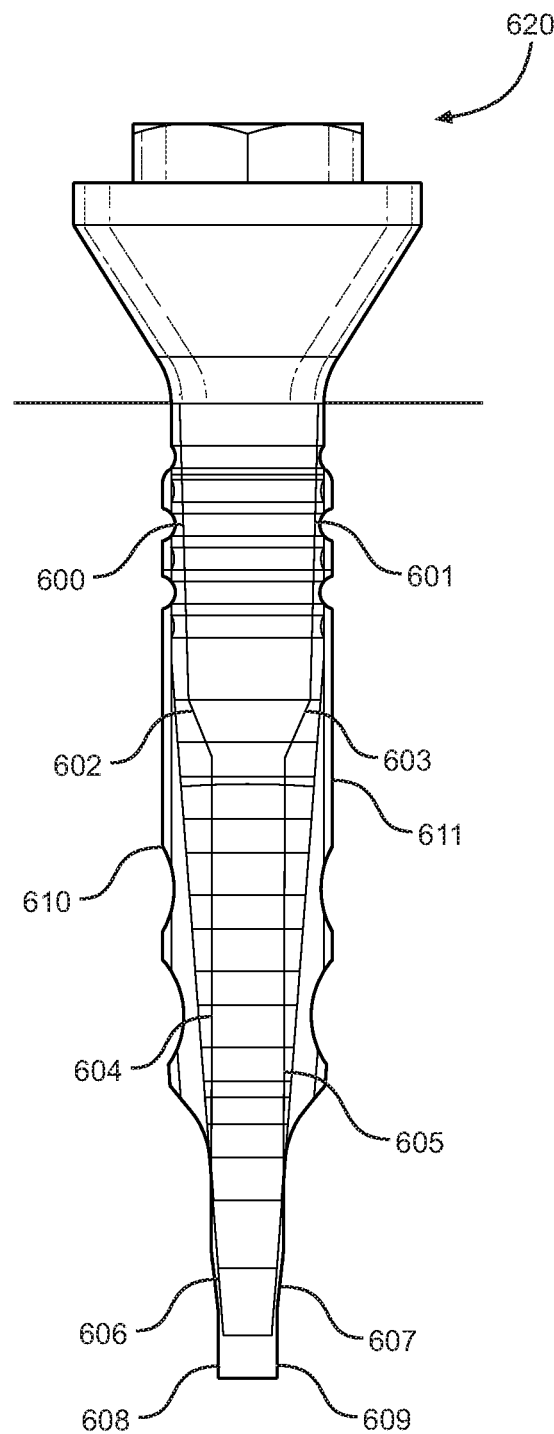
FIG. 39 is a side view in section illustrating an implant inserted into a cavity.

FIG. 39 is a view in section through the bone 120 along the line A-A of FIG. 17, and shows the osteotomy cavity sidewalls 376 (made up of reference numerals 600 to 609) and the implant 620. The sidewalls 608 and 609 may be formed with the micro-saw 160 as described above. The sidewalls 604, 605, 606, and 607 may be formed with the micro-file 170 as described above. The sidewalls 600 and 601 may be formed with the file tip 190 when the file tip 190 is inserted until the shallowest laser mark 193 reaches the top of the bone 120 at the opening of the cavity 376, as shown in FIG. 29. The terminal end faces of the file tip 190 that are equivalent to the faces 46a and 46b of the file tip 40 form the sidewalls 602 and 603 when the file tip 190 is inserted until the first (shallowest) laser marking 193 is at the opening of the osteotomy as in FIG. 29. The file tip 190 may be inserted beyond the position shown by the sidewalls 602 and 603, but the position of the sidewalls 602 and 603 is typical for the insert 620 in healthy bone. The sidewalls 602 and 603 define the necked-down region of one embodiment where the cavity tapers from the thickness between the sidewalls 600 and 601 to the thickness between the sidewalls 604 and 605.

During formation of the cavity, the pilot voids are formed and then the micro-saw is inserted until it forms the sidewalls 608 and 609 on both sides of the cavity from the extreme cortical region to the extreme apical region. Then the micro file tip 170 is inserted until it forms the sidewalls 604, 605, 606 and 607 from the extreme cortical region to the extreme apical region. Then the file tip 190 is inserted until it forms the sidewalls 600, 601, 602 and 603 along the entire width of the cavity. The cavity 376 formed with this series of bone-shaping tools has a thickness difference in the coronal region, which is at the opening of the cavity, of about 0.2 mm at the body (main walls) of the implant, and about 0.4 mm at the tips of the sagittal fins 610 and 611. This thickness difference causes a "press fit" as described above. The existence of at least one necked-down region that transitions from the thicker cavity at the opening to the thinner cavity at the apical end, may be found in the cavities created under the present invention. The press fit deeper than the necked-down region increases to 0.77 mm at the main body of the implant 620 and 1.15 mm at the sagittal fins 610 and 611. This is contrasted with the 0.46 mm press-fit for the sclerotic bone preparation shown in the embodiment of FIG. 38.

The micro-file 170 may have a tapered tip due to shaping of the metal substrate, the varying thickness of an abrasive coating, or any other reason. This may cause the formation of a tapering in the cavity as defined by two sidewalls 606 and 607 adjacent the apical end of the original sidewalls 608 and 609. Insertion of the implant 620 is as described herein.

Figure 40:
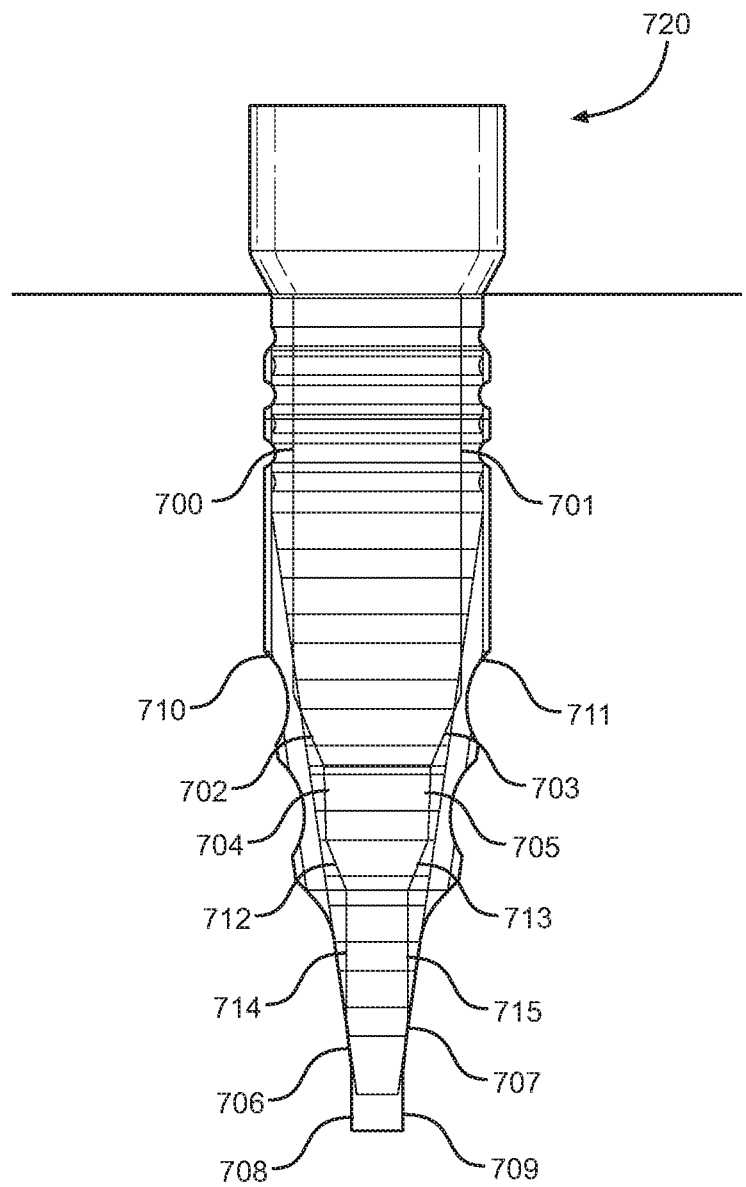
FIG. 40 is a side view in section illustrating an implant inserted into a cavity.

FIG. 40 is a view in section through the bone 120 along the line A-A of FIG. 17, and shows the osteotomy cavity sidewalls 376 (made up of reference numerals 700 to 709 and 712 to 715) and the implant 720. The sidewalls 708 and 709 may be formed with the micro-saw 16 as described above. The sidewalls 706, 707, 714 and 715 may be formed with the micro-file 170 as described above. The sidewalls 704 and 705 may be formed with the file tip 190 when the file tip 190 is inserted until the second laser mark 193 is just under the bone 120 at the opening of the cavity 376, as shown in FIG. 29. The terminal end faces of the file tip 190 that are equivalent to the faces 46a and 46b of the file tip 40 form the sidewalls 712 and 713 when the file tip 190 is inserted until the second laser marking 193 is at the opening of the osteotomy. The file tip 190 may be inserted above or beyond the position shown by the sidewalls 712 and 713, but the position of the sidewalls 712 and 713 is typical for the insert 720 in healthy bone. The sidewalls 712 and 713 define the necked-down region of one embodiment where the cavity tapers from the thickness between the sidewalls 704 and 705 to the thickness at the top of the sidewalls 706 and 707.

During formation of the cavity, the pilot voids are formed and then the micro-saw are inserted until they form the sidewalls 708 and 709 on both sides of the cavity from the extreme cortical region to the extreme apical region. Then the micro file tip 170 is inserted until it forms the sidewalls 706, 707, 714 and 715 from the extreme cortical region to the extreme apical region. Then the file tip 190 is inserted until it forms the sidewalls 704, 705, 712 and 713 along the entire width of the cavity. The cavity formed with this series of bone-shaping tools has a thickness difference in the coronal region, which is at the opening of the cavity, of about 0.6 mm at the body (main walls) of the implant, and about 0.8 mm at the tips of the sagittal fins 710 and 711. This thickness difference causes a "press fit" as described above. The existence of at least one necked-down region that transitions from the thicker cavity at the opening to the thinner cavity at the apical end, may be found in the cavities created under the present invention. The press fit that is deeper than the first necked-down region decreases to 0.41 mm at the implant 720 and 1.06 mm at the sagittal fins 710 and 711. Deeper than the second necked-down region, the press-fit increases to 0.54 mm at the implant 720 and 1.13 mm at the sagittal fins.

The micro-file 170 may have a tapered tip due to shaping of the metal substrate, the varying thickness of an abrasive coating, or any other reason. This may cause the formation of a tapering in the cavity as defined by two sidewalls 706 and 707 adjacent the apical end of the original sidewalls 708 and 709. Insertion of the implant 720 is as described herein.

Alternatively, or additionally, the cavity shown in FIG. 40 may be enlarged by the file tips 360 and/or 380, which are shown in FIGS. 30 and 31 and may be equivalent to the file tips 60 and 80, respectively, described above and shown in FIGS. 6-15. FIG. 40 shows insertion of an implant 720 that is thicker than the implant 620 of FIG. 39. Additional mesiodistal space may be created by abrading the sidewalls as determined by pre-surgical planning. Thus, the practitioner may attach the wedge-shaped file tip 360 to the hand-piece and continue to enlarge the cavity of FIG. 40 mesio-distally to the desired thickness at the desired positions along the cavity length, thereby forming the final cavity shown in FIG. 40. The surgeon may then attach the file tip 360 to the hand-piece, actuate the hand-piece in a conventional manner to vibrate, and then insert the terminal end of the file tip 360 into the cavity to its depth marking 363 as shown in FIG. 30 all along the entire width of the cavity to form the cavity shown in FIG. 40. This causes the terminal end faces of the tip 360 to form the sidewalls 702 and 703 at the desired depth in the cavity, which may be about 5.5 mm from the opening (at the opening ends of the sidewalls), and the sidewalls 700 and 701 that are slightly thicker (about 2.3 mm) than the sidewalls previously formed by the tip 190. Depending on the amount of bone mineralization at the implant site, this step may not be necessary. However, failure to provide proper mesiodistal space in the cavity may increase the risk of iatrogenic bone fracture, as will be understood by the person of ordinary skill.

The sidewalls of the osteotomy in FIG. 40 that correspond to the faces of the file tip 360 are the sidewalls 700 and 701, which are formed by the faces of the file tip 360 that are equivalent to the sidewalls 64a and 64b of the tip 60 described above. The sidewalls 702 and 703 are formed by the faces of the file tip 360 that are equivalent to the sidewalls 66a and 66b of the tip 60 described above. Of course, the file tip 360 may be inserted more or less than the depth that the sidewalls 700, 701, 702 and 703 are shown extending in FIG. 40, and this will be determined by the surgeon. If the tip 360 is the last tip inserted into the cavity, there is a necked down region formed by the sidewalls 702 and 703.

Figure 41:
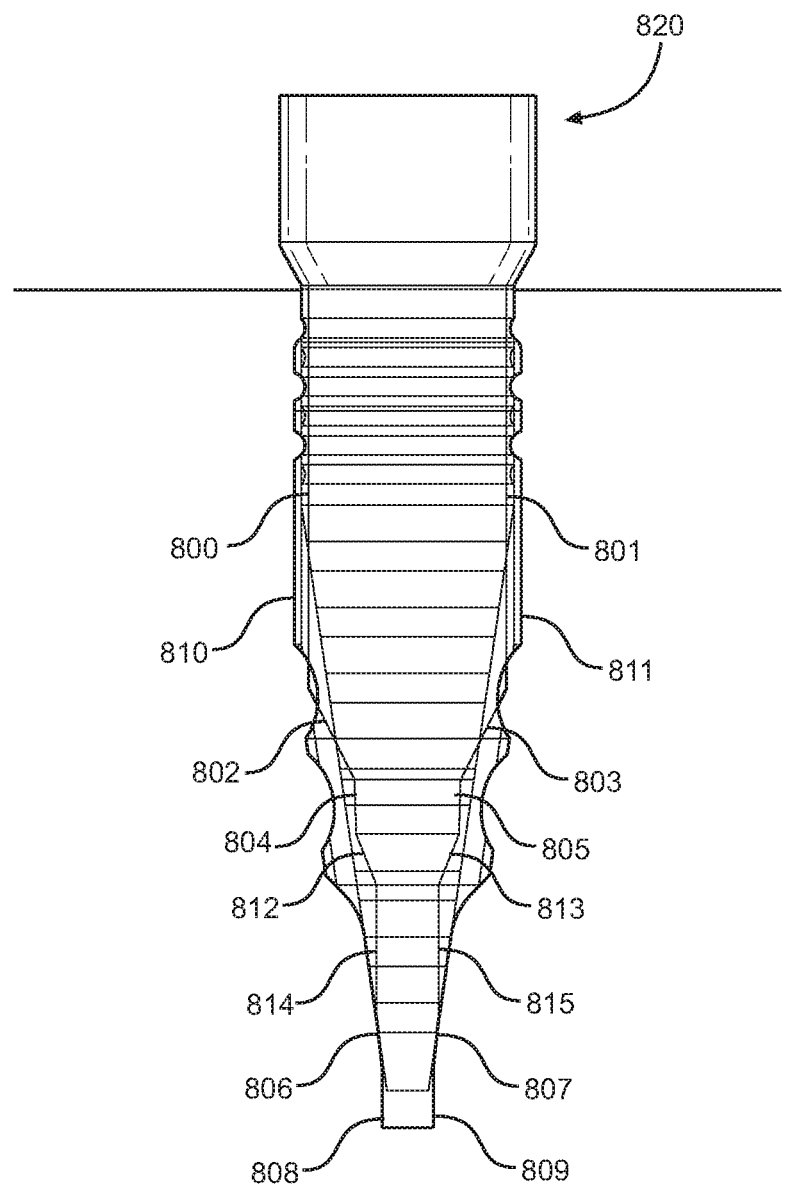
FIG. 41 is a side view in section illustrating an implant inserted into a cavity.

FIG. 41 is a view in section through the bone 120 along the line A-A of FIG. 17, and shows the osteotomy cavity sidewalls 376 (made up of reference numerals 800 to 809 and 812 to 815) and the implant 820. The sidewalls 808 and 809 may be formed with the micro-saw 160 as described above. The sidewalls 806, 807, 814 and 815 may be formed with a micro file 170 as described above. The sidewalls 804 and 805 may be formed with the file tip 190 when the file tip 190 is inserted until the shallowest laser mark 193 reaches the top of the bone 120 at the opening of the finished cavity 376, as shown in FIG. 29. The terminal end faces of the file tip 190 that are equivalent to the faces 46a and 46b of the file tip 40 form the sidewalls 812 and 813 when the file tip 190 is inserted until the second laser marking 193 is below the opening of the osteotomy. The file tip 190 may be inserted beyond the position shown by the sidewalls 812 and 813, but the position of the sidewalls 812 and 813 is typical for the implant 820 in healthy bone. The sidewalls 812 and 813 define the necked-down region of one embodiment where the cavity tapers from the thickness between the sidewalls 804 and 805 to the thickness at the top of the sidewalls 814 and 815.

During formation of the cavity, the pilot voids are formed and then the micro-saw is inserted until they form the sidewalls 808 and 809 on both sides of the cavity from the extreme cortical region to the extreme apical region. Then the micro file tip 170 is inserted until it forms the sidewalls 806 807, 814 and 815 from the extreme cortical region to the extreme apical region. Then the file tip 190 is inserted until it forms the sidewalls 804, 805, 812 and 813 along the entire width of the cavity. The cavity formed with this series of bone-shaping tools has a thickness difference in the coronal region, which is at the opening of the cavity, of about 0.2 mm at the body (main walls) of the implant, and about 0.4 mm at the tips of the sagittal fins 810 and 811. This thickness difference causes a "press fit" as described above. The existence of at least one necked-down region that transitions from the thicker cavity at the opening to the thinner cavity at the apical end, may be found in the cavities created under the present invention. The press fit deeper than the first necked-down region decreases to 0.32 mm at the main body of the implant 820 and 0.77 mm at the sagittal fins 810 and 811. Deeper than the second necked-down region, the press-fit increases slightly to 0.54 mm at the main body of the implant 820 and 1.13 mm at the sagittal fins.

The micro-file 170 may have a tapered tip due to shaping of the metal substrate, the varying thickness of an abrasive coating, or any other reason. This may cause the formation of a tapering in the cavity as defined by two sidewalls 806 and 807 adjacent the apical end of the original sidewalls 808 and 809. This tapering may cause a friction fit between the implant and bone in this region. Insertion of the implant 820 is as described herein.

Alternatively, or additionally, the cavity shown in FIG. 41 may be enlarged by the file tips 360 and/or 380, which are shown in FIGS. 30 and 31 and may be equivalent to the file tips 60 and 80, respectively, described above and shown in FIGS. 6-15. FIG. 41 shows insertion of an implant 820 that is thicker than the implant 620 of FIG. 39. Additional mesiodistal space may be created by abrading the sidewalls as determined by pre-surgical planning. Thus, the practitioner may attach the wedge-shaped file tips 360 and/or 380 to the hand-piece and continue to enlarge the cavity of FIG. 41 mesiodistally to the desired thickness at the desired positions along the cavity length, thereby forming the final cavity shown in FIG. 41. The surgeon may then attach the file tip 360 and/or 380 to the hand-piece, actuate the hand-piece in a conventional manner to vibrate, and then insert the terminal end of the file tips 360 and/or 380 into the cavity to its depth markings 363 and/or 383 as shown in FIG. 30 all along the entire width of the cavity to form the cavity shown in FIG. 41. This causes the terminal end faces of the tip 380 to form the sidewalls 802 and 803 at the desired depth in the cavity, which may be about 5.5 mm from the opening (at the opening ends of the sidewalls), and the sidewalls 800 and 801 that are thicker (about 2.7 mm) than the sidewalls previously formed by the tip 190. Depending on the amount of bone mineralization at the implant site, this step may not be necessary. However, failure to provide proper mesiodistal space in the cavity may increase the risk of iatrogenic bone fracture, as will be understood by the person of ordinary skill.

The sidewalls of the osteotomy in FIG. 41 that correspond to the faces of the file tip 380 are the sidewalls 800 and 801, which are formed by the faces of the file tip 380 that are equivalent to the sidewalls 84a and 84b of the tip 80 described above. The sidewalls 802 and 803 are formed by the faces of the file tip 360 that are equivalent to the sidewalls 86a and 86b of the tip 80 described above. Of course, the file tip 380 may be inserted more or less than the depth that the sidewalls 800, 801, 802 and 803 are shown extending in FIG. 41, and this will be determined by the surgeon. If the tip 380 is the last tip inserted into the cavity, there is a second necked down region formed by the sidewalls 802 and 803.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:
1. An osteotomy method comprising:
 (a) forming an elongated cavity in a bone, the cavity defined by spaced sidewalls and having:
  (i) a cavity length and a cavity width that are greater than a cavity thickness;
  (ii) an opening end in a cortical region of the bone;
  (iii) an apical end in a trabecular region of the bone;
  (iv) a longitudinal axis extending between the opening end and the apical end and a non-circular cross section through a plane perpendicular to the longitudinal axis;
 (b) attaching a first removable tip to an instrument that is configured to vibrate the first tip at ultrasonic frequency, the first tip having a base that attaches to the instrument and a tip shaft extending from the base to a working portion, the working portion comprising:

(i) first and second opposing faces defining the terminal end of the first tip and forming an angle relative to one another between about 45 degrees and about degrees;
(ii) third and fourth opposing faces disposed between the first and second faces and the base, the third and fourth faces angled relative to one another between about 0.0 degrees and about 25 degrees;
(iii) wherein said at least first and second faces have surface formations that result in the abrasion of bone when any of said faces contacts bone during vibration;
(c) inserting the working portion of the first tip into the cavity and seating the at least first and second faces against the cavity sidewalls while the instrument vibrates the first tip, thereby abrading the sidewalls to make the cavity thickness greater at the opening end than at the apical end and form at least a first necked-down portion over a first segment of the cavity length in which a first per unit length change in cavity thickness in the first segment's length exceeds a per unit length change in cavity thickness along the cavity length.

2. The osteotomy method in accordance with claim 1, further comprising:
(a) attaching a second removable tip to an instrument that is configured to vibrate the second tip at ultrasonic frequency, the second tip having a base that attaches to the instrument and a tip shaft extending from the base to a working portion, the working portion comprising:
(i) first and second opposing faces defining the terminal end of the second tip and forming an angle relative to one another between about 45 degrees and about 90 degrees;
(ii) third and fourth opposing faces disposed between the first and second faces and the base, the third and fourth faces angled relative to one another between about 0.0 degrees and about 2 degrees;
(iii) wherein said at least first and second faces have surface formations that result in the abrasion of bone when one of said faces contacts bone during vibration;
(b) inserting the working portion of the second tip into the cavity and seating the first and second faces against the cavity sidewalls while the instrument vibrates the second tip, thereby making the cavity thickness greater at the first necked-down portion.

3. The osteotomy method in accordance with claim 1, further comprising:
(a) attaching a second removable tip to an instrument that is configured to vibrate the second tip at ultrasonic frequency, the second tip having a base that attaches to the instrument and a tip shaft extending from the base to a working portion, the working portion comprising:
(i) first and second opposing faces defining the terminal end of the second tip and forming an angle relative to one another between about 45 degrees and about 90 degrees;
(ii) third and fourth opposing faces disposed between the first and second faces and the base, the third and fourth faces angled relative to one another between about 0.0 degrees and about 2 degrees;
(iii) wherein said at least first and second faces have surface formations that result in the abrasion of bone when one of said faces contacts bone during vibration;
(b) inserting the working portion of the second tip into the cavity and seating the first and second faces against the cavity sidewalls while the instrument vibrates the second tip, thereby abrading the sidewalls to form a second necked-down portion over a second segment of the cavity length in which a second per unit length change in cavity thickness in the second segment's length exceeds a per unit length change in cavity thickness along the cavity length.

4. The osteotomy method in accordance with claim 1, further comprising inserting an implant into the cavity, thereby compressing the trabecular bone at the first necked-down portion.

5. The osteotomy method in accordance with claim 4, further comprising driving the implant longitudinally into the cavity by rapidly impacting the implant.

* * * * *

UNITED STATES PATENT AND TRADEMARK OFFICE
CERTIFICATE OF CORRECTION

PATENT NO. : 12,114,870 B1
APPLICATION NO. : 15/940275
DATED : October 15, 2024
INVENTOR(S) : Tomaso Vercellotti and Alberto Rebaudi Page 1 of 1

It is certified that error appears in the above-identified patent and that said Letters Patent is hereby corrected as shown below:

In the Claims

In Column 27; Line 4, insert --90-- before the word "degrees".

Signed and Sealed this
Thirty-first Day of December, 2024

Derrick Brent
*Acting Director of the United States Patent and Trademark Office*